United States Patent
Kuduk et al.

(10) Patent No.: US 9,994,570 B2
(45) Date of Patent: Jun. 12, 2018

(54) BRIDGED DIAZEPANE OREXIN RECEPTOR ANTAGONISTS

(71) Applicant: MERCK SHARP & DOHME CORP., Rahway, NJ (US)

(72) Inventors: Scott D. Kuduk, Harleysville, PA (US); Thomas S. Reger, Lansdale, PA (US); Anthony J. Roecker, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 15/529,769

(22) PCT Filed: Nov. 20, 2015

(86) PCT No.: PCT/US2015/061732
§ 371 (c)(1),
(2) Date: May 25, 2017

(87) PCT Pub. No.: WO2016/085783
PCT Pub. Date: Jun. 2, 2016

(65) Prior Publication Data
US 2017/0320876 A1 Nov. 9, 2017

Related U.S. Application Data

(60) Provisional application No. 62/084,966, filed on Nov. 26, 2014.

(51) Int. Cl.
*C07D 471/08* (2006.01)
*A61K 31/437* (2006.01)
*A61K 31/506* (2006.01)

(52) U.S. Cl.
CPC .................. *C07D 471/08* (2013.01)

(58) Field of Classification Search
CPC ... A61K 31/437; A61K 31/506; C07D 471/08
USPC ............. 514/275, 256; 544/331, 332
See application file for complete search history.

(56) References Cited

U.S. PATENT DOCUMENTS

| | | | |
|---|---|---|---|
| 7,834,015 B2 | 11/2010 | Jones et al. |
| 7,951,797 B2 | 5/2011 | Breslin et al. |
| 8,242,121 B2 | 8/2012 | Coleman et al. |
| 8,263,586 B2 | 9/2012 | Cox et al. |
| 8,349,872 B2 | 1/2013 | Coleman et al. |
| 8,357,700 B2 | 1/2013 | Cox et al. |
| 8,357,709 B2 | 1/2013 | Coleman et al. |
| 8,362,009 B2 | 1/2013 | Bergman et al. |
| 8,399,494 B2 | 3/2013 | Bergman et al. |
| 8,466,281 B2 | 6/2013 | Coleman et al. |
| 8,618,102 B2 | 12/2013 | Coleman et al. |
| 8,623,863 B2 | 1/2014 | Coleman et al. |
| 8,669,272 B2 | 3/2014 | Breslin et al. |
| 8,685,961 B2 | 4/2014 | Brashear et al. |
| 8,710,076 B2 | 4/2014 | Breslin et al. |
| 8,940,898 B2 | 1/2015 | Kuduk et al. |
| 9,029,364 B2 | 5/2015 | Kuduk et al. |
| 9,156,819 B2 | 10/2015 | Kuduk et al. |
| 9,546,152 B2 | 1/2017 | Kuduk et al. |
| 9,550,786 B2 | 1/2017 | Cooke et al. |
| 9,556,145 B2 | 1/2017 | Kuduk et al. |
| 9,556,190 B2 | 1/2017 | Kuduk et al. |
| 9,586,934 B2 | 3/2017 | Kuduk et al. |
| 9,586,950 B2 | 3/2017 | Kuduk et al. |
| 9,617,246 B2 | 4/2017 | Kuduk et al. |
| 9,624,197 B2 | 4/2017 | Kuduk et al. |
| 2009/0239843 A1 | 9/2009 | Coleman et al. |
| 2010/0029736 A1 | 2/2010 | Cox et al. |
| 2011/0195957 A1 | 8/2011 | Bergman et al. |
| 2012/0196901 A1 | 8/2012 | Coleman et al. |
| 2015/0322039 A1 | 11/2015 | Kuduk et al. |
| 2015/0322040 A1 | 11/2015 | Kuduk et al. |
| 2015/0322041 A1 | 11/2015 | Kuduk et al. |
| 2016/0016935 A1 | 1/2016 | Kuduk et al. |
| 2016/0068510 A1 | 3/2016 | Kuduk et al. |
| 2016/0068514 A1 | 3/2016 | Kuduk |
| 2016/0102073 A1 | 4/2016 | Kuduk et al. |
| 2016/0176858 A1 | 6/2016 | Liverton et al. |
| 2016/0185768 A1 | 6/2016 | Liverton et al. |

(Continued)

FOREIGN PATENT DOCUMENTS

WO WO2016069510 5/2016
WO WO2016069512 5/2016

(Continued)

OTHER PUBLICATIONS

Anthony J. Roecker et al, Orexin Receptor Antagonists: New Therapeutic Agents for the Treatment of Insomnia, Journal of Medicinal Chemistry, 2016, 504-530, 59(2).

Coleman et al, Design and Synthesis of Conformationally Constrained N,N Disubstituted 1,4-Diazepanes as Potent Orexin Receptor Antagonists, Bioorganic & Medicinal Chemistry Letters, 2010, 2311-2315, 20(7).

Jason W. Skudlarek et al, Investigation of orexin-2 selective receptor antagonists: Structural modifications resulting in dual orexin receptor antagonists, Bioorganic & Medicinal Chemistry Letters, 2017, 1364-1370, 27(6).

(Continued)

*Primary Examiner* — Brenda L Coleman
(74) *Attorney, Agent, or Firm* — J. Eric Thies; John C. Todaro

(57) ABSTRACT

The present invention is directed to bridged diazepane compounds which are antagonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

12 Claims, No Drawings

(56) References Cited

U.S. PATENT DOCUMENTS

2016/0304490 A1    10/2016   Kuduk et al.
2016/0318900 A1    11/2016   Kuduk et al.
2016/0318923 A1    11/2016   Kuduk et al.

FOREIGN PATENT DOCUMENTS

| WO | WO2016069515 | 5/2016 |
| WO | WO2016069517 | 5/2016 |
| WO | WO2016069519 | 5/2016 |
| WO | WO2016085783 | 6/2016 |
| WO | WO2016085784 | 6/2016 |
| WO | WO2016089721 | 6/2016 |
| WO | WO2016089722 | 6/2016 |
| WO | WO2016100154 | 6/2016 |
| WO | WO2016100156 | 6/2016 |
| WO | WO2016100157 | 6/2016 |
| WO | WO2016100161 | 6/2016 |
| WO | WO2016100162 | 6/2016 |
| WO | WO2016106105 | 6/2016 |
| WO | WO2016106106 | 6/2016 |

OTHER PUBLICATIONS

National Center for Biotechnology Information. PubChem Substance Database; SID=137865873, https://pubchem.ncbi.nlm.nih.gov/substance/137865873 (accessed Jun. 30, 2016).

BRIDGED DIAZEPANE OREXIN RECEPTOR ANTAGONISTS

CROSS REFERENCE TO RELATED APPLICATIONS

This application is a U.S. National Phase application under 35 U.S.C. § 371 of PCT Application No. PCT/US2015/061732, filed Nov. 20, 2015, which claims priority under 35 U.S.C. § 119(e) from U.S. application Ser. No. 62/084,966, filed Nov. 26, 2014.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R.M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX1 receptor and OX2 receptor as the two subtypes of orexin receptors.

SUMMARY OF THE INVENTION

The present invention is directed to bridged diazepane compounds which are antagonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

DETAILED DESCRIPTION OF THE INVENTION

The present invention is directed to compounds of the formula I:

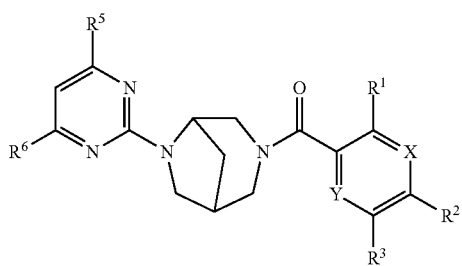

I wherein:
X is CH or N;
Y is CH or N;
$R^1$ is selected from the group consisting of:
(1) hydrogen,
(2) halogen,
(3) hydroxyl,
(4) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from $R^4$,
(5) —(C=O)O$_m$—O$_n$—C$_{3-6}$cycloalkyl, where the cycloalkyl is unsubstituted or substituted with one or more substituents selected from $R^4$,
(6) —(C=O)$_m$—C$_{2-4}$alkenyl, where the alkenyl is unsubstituted or substituted with one or more substituents selected from $R^4$,
(7) —(C=O)$_m$—C$_{2-4}$alkynyl, where the alkynyl is unsubstituted or substituted with one or more substituents selected from $R^4$,
(8) —(C=O)$_m$—O$_n$-phenyl or —(C=O)$_m$—O$_n$-naphthyl, where the phenyl or naphthyl is unsubstituted or substituted with one or more substituents selected from $R^4$,
(9) —(C=O)$_m$—O$_n$-heterocycle, where the heterocycle is unsubstituted or substituted with one or more substituents selected from $R^4$,
(10) —(C=O)$_m$—NR$^{10}$R$^{11}$, wherein R$^{10}$ and R$^{11}$ are independently selected from the group consisting of:
(a) hydrogen,
(b) C$_{1-6}$alkyl, which is unsubstituted or substituted with $R^4$,
(c) C$_{3-6}$alkenyl, which is unsubstituted or substituted with $R^4$,
(d) C$_{3-6}$alkynyl, which is unsubstituted or substituted with $R^4$,
(e) C$_{3-6}$cycloalkyl which is unsubstituted or substituted with $R^4$,
(f) phenyl, which is unsubstituted or substituted with $R^4$, and
(g) heterocycle, which is unsubstituted or substituted with $R^4$,
(11) —S(O)$_2$—NR$^{10}$R$^{11}$,
(12) —S(O)$_q$—R$^{12}$, where q is 0, 1 or 2 and where R$^{12}$ is selected from the definitions of R$^{10}$ and R$^{11}$,
(13) —CO$_2$H,
(14) —CN, and
(15) —NO$_2$;
$R^2$ is selected from the group consisting of:
(1) hydrogen,
(2) hydroxyl,
(3) halogen, and
(4) C$_{1-6}$alkyl;
$R^3$ is selected from the group consisting of:
(1) hydrogen,
(2) hydroxyl,
(3) halogen, and
(4) C$_{1-6}$alkyl;
$R^4$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH$_2$,
(8) —NH—C$_{1-6}$alkyl, (9) —NO$_2$,
(10) phenyl,
(11) heterocycle,
(12) —CO$_2$H, and
(13) —CN;

R$^5$ is selected from the group consisting of:
(1) halogen,
(2) —CN, and
(3) C$_{1-6}$alkyl;

R$^6$ is selected from the group consisting of:
(1) halogen,
(2) —CN, and
(3) C$_{1-6}$alkyl;

or a pharmaceutically acceptable salt thereof.

An embodiment of the present invention includes compounds of the formula Ia:

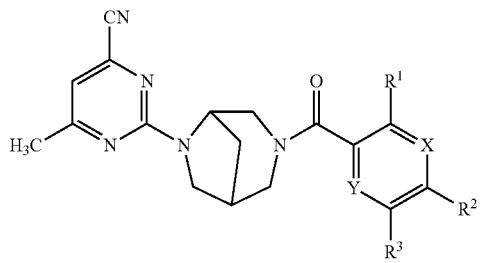

wherein R$^1$, R$^2$, R$^3$, X and Y are defined herein; or a pharmaceutically acceptable salt thereof.

An embodiment of the present invention includes compounds of the formula Ia':

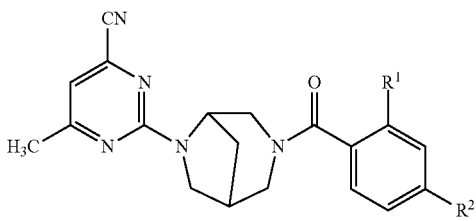

wherein R$^1$ and R$^2$ are defined herein; or a pharmaceutically acceptable salt thereof.

An embodiment of the present invention includes compounds of the formula Ia'':

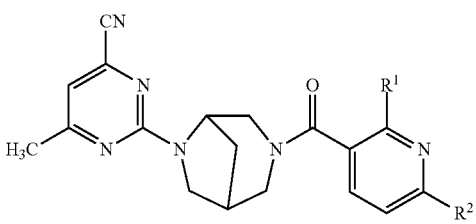

wherein R$^1$ and R$^2$ are defined herein; or a pharmaceutically acceptable salt thereof.

An embodiment of the present invention includes compounds of the formula Ia''':

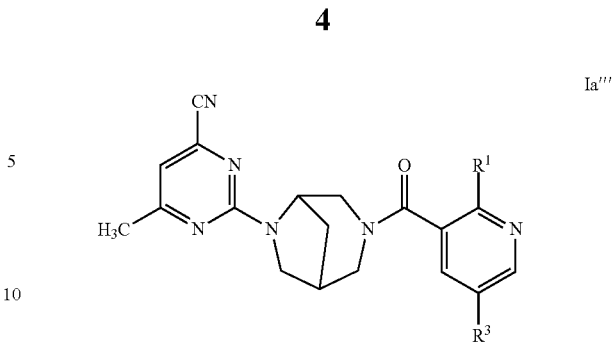

wherein R$^1$ and R$^3$ are defined herein; or a pharmaceutically acceptable salt thereof.

An embodiment of the present invention includes compounds of the formula Ia'''':

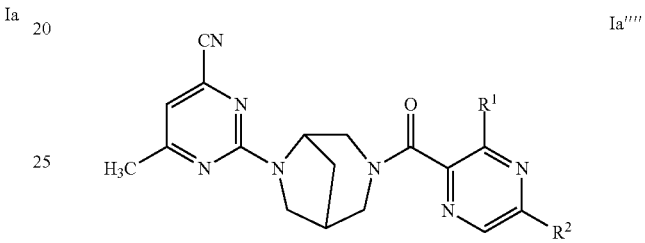

wherein R$^1$ and R$^2$ are defined herein; or a pharmaceutically acceptable salt thereof.

An embodiment of the present invention includes compounds of the formula Ib:

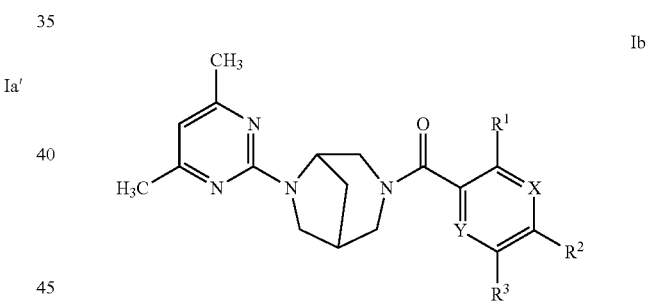

wherein R$^1$, R$^2$, R$^3$, X and Y are defined herein; or a pharmaceutically acceptable salt thereof.

An embodiment of the present invention includes compounds of the formula Ib':

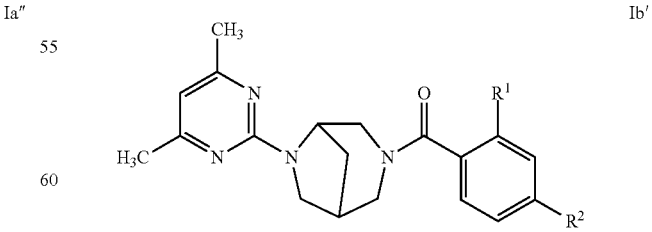

wherein R$^1$ and R$^2$ are defined herein; or a pharmaceutically acceptable salt thereof.

An embodiment of the present invention includes compounds of the formula Ib'':

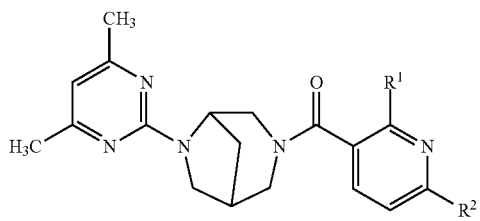

Ib″ wherein R¹ and R² are defined herein; or a pharmaceutically acceptable salt thereof.

An embodiment of the present invention includes compounds of the formula Ib′″:

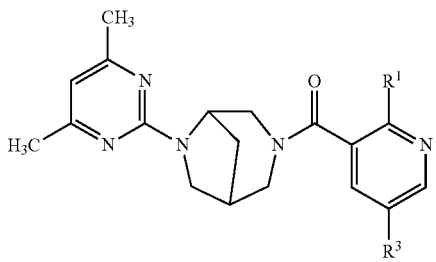

Ib′″ wherein R¹ and R³ are defined herein; or a pharmaceutically acceptable salt thereof.

An embodiment of the present invention includes compounds of the formula Ib″″:

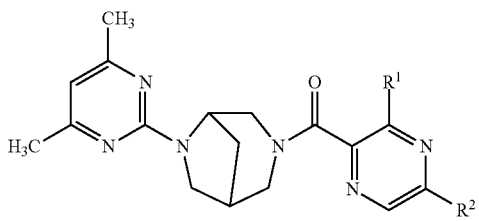

Ib″″ wherein R¹ and R² are defined herein; or a pharmaceutically acceptable salt thereof.

An embodiment of the present invention includes compounds wherein X is N.

An embodiment of the present invention includes compounds wherein X is CH.

An embodiment of the present invention includes compounds wherein Y is N.

An embodiment of the present invention includes compounds wherein Y is CH.

An embodiment of the present invention includes compounds wherein R¹ is selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl,
(6) heteroaryl, wherein heteroaryl is selected from imidazolyl, indolyl, oxazolyl, pyridyl, pyrrolyl, pyrimidinyl, tetrazolyl, and triazolyl, which is unsubstituted or substituted with halogen, hydroxyl, $C_{1-6}$alkyl, —O—$C_{1-6}$alkyl or —NO₂,
(7) phenyl, which is unsubstituted or substituted with halogen, hydroxyl, $C_{1-6}$alkyl, —O—$C_{1-6}$alkyl or —NO₂,
(8) —O-phenyl, which is unsubstituted or substituted with halogen, hydroxyl, $C_{1-6}$alkyl, —O—$C_{1-6}$alkyl or —NO₂,
(9) —CN, and
(10) —NH—$C_{1-6}$alkyl, or —N($C_{1-6}$alkyl)($C_{1-6}$alkyl), which is unsubstituted or substituted with halogen, hydroxyl, $C_{1-6}$alkyl, and —O—$C_{1-6}$alkyl.

An embodiment of the present invention includes compounds wherein R¹ is selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl,
(6) —CN, and
(7) heteroaryl, wherein heteroaryl is selected from imidazolyl, indolyl, oxazolyl, pyridyl, pyrrolyl, pyrimidinyl, tetrazolyl, and triazolyl, which is unsubstituted or substituted with halogen, hydroxyl, $C_{1-6}$alkyl, —O—$C_{1-6}$alkyl or —NO₂.

An embodiment of the present invention includes compounds wherein R¹ is selected from the group consisting of:
(1) hydrogen,
(2) halogen,
(3) $C_{1-6}$alkyl, which is unsubstituted or substituted with halogen,
(4) —O—$C_{1-6}$alkyl, which is unsubstituted or substituted with halogen,
(5) —CN, and
(6) heteroaryl, wherein heteroaryl is selected from imidazolyl, indolyl, oxazolyl, pyridyl, pyrrolyl, pyrimidinyl, tetrazolyl, and triazolyl.

An embodiment of the present invention includes compounds wherein R¹ is independently selected from the group consisting of:
(1) hydrogen,
(2) fluoro,
(3) chloro,
(4) bromo,
(5) methyl,
(6) ethyl,
(7) methoxy,
(8) trifluoromethyl,
(9) trifluoromethoxy,
(10) difluoromethoxy,
(11) difluoroethoxy,
(12) trifluoroethoxy, and
(13) heteroaryl, wherein heteroaryl is selected from imidazolyl, indolyl, oxazolyl, pyridyl, pyrrolyl, pyrimidinyl, tetrazolyl, and triazolyl.

An embodiment of the present invention includes compounds wherein R¹ is selected from the group consisting of:
(1) hydrogen,
(2) fluoro,
(3) chloro,
(4) methyl,
(5) methoxy,
(6) trifluoromethoxy,
(7) difluoromethoxy, (8) difluoroethoxy,
(9) trifluoroethoxy, and
(10) tetrazolyl, and
(11) triazolyl.

An embodiment of the present invention includes compounds wherein $R^2$ is selected from the group consisting of:
(1) hydrogen, and
(2) fluoro.

An embodiment of the present invention includes compounds wherein $R^2$ is hydrogen.

An embodiment of the present invention includes compounds wherein $R^3$ is selected from the group consisting of:
(1) hydrogen, and
(2) fluoro.

An embodiment of the present invention includes compounds wherein $R^3$ is hydrogen.

An embodiment of the present invention includes compounds wherein $R^5$ is methyl or —CN. An embodiment of the present invention includes compounds wherein $R^6$ is methyl. An embodiment of the present invention includes compounds wherein $R^5$ is methyl and $R^6$ is methyl. An embodiment of the present invention includes compounds wherein $R^5$ is —CN and $R^6$ is methyl.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

The present invention is also directed to the use of the compounds disclosed herein as antagonists of orexin receptor activity. The subject compounds and pharmaceutically acceptable salts thereof are useful in a method of antagonizing orexin receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for antagonizing orexin receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to antagonize the orexin receptor in the subject. In an embodiment, the amount of compound can be an "effective amount", wherein the subject compound is administered in an amount that will elicit the biological or medical response of a tissue, system, animal or human that is being sought by the researcher, veterinarian, medical doctor or other clinician. An effective amount does not necessarily include considerations of toxicity and safety related to the administration of the compound. It is recognized that one skilled in the art may affect neurological and psychiatric disorders associated with orexin receptor activation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and or "administering a" compound should be understood to mean providing a compound of the invention or a prodrug of a compound of the invention to to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 µg/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% CO2. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 µl assay buffer and then incubated for 60 min (37° C., 5% CO2) in 60 µl assay buffer containing 1 µM Fluo-4AM ester, 0.02% pluronic acid, and 1% BSA. The dye loading solution is then aspirated and cells are washed 3 times with 100 µl assay buffer. 30 µl of that same buffer is left in each well. Within the Fluorescent Imaging Plate Reader (FLIPR, Molecular Devices), test compounds are added to the plate in a volume of 25 μl, incubated for 5 min and finally 25 μl of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. Alternatively, compound potency can be assessed by a radioligand binding assay (described in Bergman et. al. Bioorg. Med. Chem. Lett. 2008, 18, 1425-1430) in which the inhibition constant ($K_i$) is determined in membranes prepared from CHO cells expressing either the OX1 or OX2 receptor. The intrinsic orexin receptor antagonist activity of a compound which may be used in the present invention may be determined by these assays.

All of the final compounds of the following examples had activity in antagonizing the human orexin-2 receptor in the aforementioned assays with an $IC_{50}$ of about 1 nM to 2500 nM. All of the final compounds of the following examples had activity in the FLIPR assay with an IC50 of about 5 nM to 500 nM against the orexin-2 receptor. Additional data is provided in the following Examples. Such a result is indicative of the intrinsic activity of the compounds in use as antagonists of orexin-1 receptor and/or the orexin-2 receptor. In general, one of ordinary skill in the art would appreciate that a substance is considered to effectively antagonize the orexin receptor if it has an IC50 of less than about 50 μM, or more specifically less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer;

cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seizures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

Thus, in certain embodiments the present invention may provide methods for: enhancing the quality of sleep; augmenting sleep maintenance; increasing REM sleep; increasing stage 2 sleep; decreasing fragmentation of sleep patterns; treating insomnia and all types of sleep disorders; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major depression disorder; treating or controlling bipolar disorder; or treating, controlling, ameliorating or reducing the risk of schizophrenia, in a mammalian subject which comprises administering to the subject a compound of the present invention.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the patient's weight, special diets then being followed by a subject, concurrent medication, and other factors which those skilled in the art will recognize. Generally, dosage levels of between 0.0001 to 10 mg/kg. of body weight daily are administered to the subject, e.g., humans and elderly humans, to obtain effective antagonism of orexin receptors. The dosage range will generally be about 0.5 mg to 1.0 g. per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 Hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, such as suvorexant, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414,002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those discribed in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex ®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide., (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors, such as verubecstat; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; GABAA inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art (e.g. PCT Patent Publications WO2007/126935, WO2008/008517, WO2008/008518, WO2008/069997, WO2008/143856, WO2009/058238, WO2012/148553, and WO2013/169610) or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DCM: dichloromethane; DCE: dichloroethane; DEAD: diethylazodicarboxylate; DIPEA: N,N-diisopropylethylamine; DMF: N,N-dimethylformamide; DMSO: dimethylsulfoxide; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HCl: hydrogen chloride; HOAt: 1-hydroxy-7-azabenzotriazole; HOBT: hydroxybenzotriazole hydrate; HPLC: high performance liquid chromatography; Hunig's base: N,N-diisopropylethylamine; MeOH: methanol; $MgSO_4$: magnesium sulfate; MTBE: methyl tert-butyl ether; $NaHCO_3$: sodium bicarbonate; NaOH: sodium hydroxide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; THF: tetrahydrofuran; TFA: trifluoracetic acid; X-Phos: 2-(dicyclohexyl-phosphino)-2',4',6'-triisopropylbiphenyl. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATES

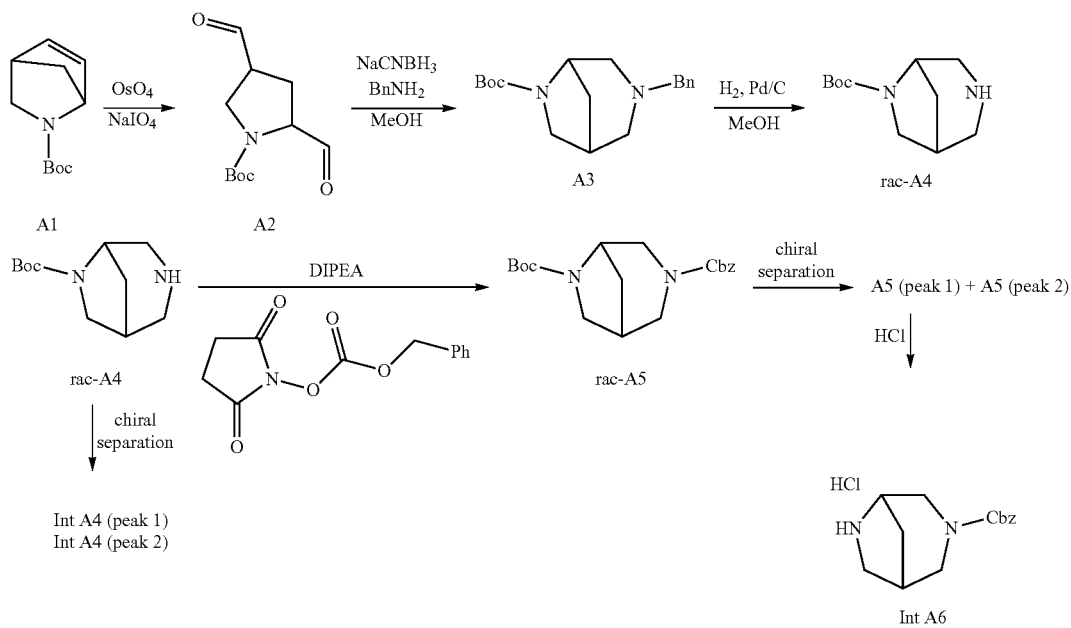

tert-butyl 3,6-diazabicyclo[3.2.1]octane-6-carboxylate (Intermediate A4 (peak 1))

benzyl 3,6-diazabicyclo[3.2.1]octane-3-carboxylate hydrochloride (Intermediate A6)

Step 1: tert-butyl 2,4-diformylpyrrolidine-1-carboxylate

To a solution of compound A1 (150 g, 0.77 mol) and pyridine (0.3 g) in THF (750 mL) and was added a solution of $OsO_4$ (7.5 g, 29.53 mmol) in water (2 L) at 10° C. To this was added $NaIO_4$ (345 g, 1.61 mol) in portions at 20° C. The resulting solution was stirred for 1.5 h at room temperature. The resulting solution was diluted with water (2 L), and extracted with EtOAc (3×1.5 L). The combined organic layers were washed with of brine (2 L), dried over $Na_2SO_4$ and concentrated under vacuum to obtain compound A2 as an oil.

Step 2: tert-butyl 3-benzyl-3,6-diazabicyclo[3.2.1]octane-6-carboxylate

The solution of compound A2 (175 g, 0.77 mol) in MeOH (2 L) was cooled to 0° C., benzylamine (92, 0.86 mol) and $NaCNBH_3$ (220 g, 3.49 mol) were added to the solution. The ice-bath was removed and the reaction stirred at room temperature overnight. The reaction mixture was concentrated and the crude residue was diluted with water (1.0 L) and extracted with EtOAc (3×500 mL). The combined organic layers were washed with aqueous $NaHCO_3$ and brine, dried over $Na_2SO_4$, concentrated and purified by silica gel chromatography to give compound A3 as an oil.

Step 3: tert-butyl 3,6-diazabicyclo[3.2.1]octane-6-carboxylate

To a solution of compound A3 (110 g, 364 mmol) in MeOH (1.5 L) was added Pd/C (10 g) under Ar. The suspension was degassed under vacuum and purged with $H_2$ several times. The mixture was stirred under $H_2$ (50 psi), at 50° C. for 2 d. The mixture was cooled to room temperature and filtered through Celite. The filtrate was concentrated to give rac-A4.

Step 4: Chiral Separation of rac-A4

176.0 g of rac-A4 was separated by SFC to provide 66.5 g of the faster eluting isomer and 69.2 g of the slower eluting isomer. The faster eluting isomer Intermediate A4 (peak 1) was utilized for further chemistry. MS (ESI) m/e: 213.1 (M+H). The following preparative conditions were used: Column: ChiralPak IC, 10 um, 300×50 mm I.D., 38° C. Mobile Phase: 40% isopropanol/60% $CO_2$, 200 mL/min, Detection: 220 nM Step 5: 3-benzyl 6-tert-butyl 3,6-diazabicyclo[3.2.1]octane-3,6-dicarboxylate A solution of rac-A4 (8.0 g, 37.7 mmol), N-(benzyloxycarbonyloxy)succinimide (9.9 g, 40 mmol), and Hunig's base (7.9 mL, 45.2 mmol) in $CH_2Cl_2$ (75 mL) was stirred at room temperature for 4 d. The reaction was concentrated and the crude material was purified by silica gel chromatography (330 g $SiO_2$, 10-65% EtOAc/hexanes, 50 min gradient) to give rac-A5 as an oil. MS (ESI) m/e: 347.2 (M+H).

Step 6: Chiral Separation of rac-A5

12.6 g of rac-A5 was separated by SFC and the second eluting isomer A5 (peak 2) was utilized for further chemistry. The following preparative conditions were used: Column: ChiralPak AD-H, 3 cm i.d.×25 cm length, Mobile Phase: 10% MeOH/90% $CO_2$+0.1% diethylamine, 80 mL/min, Detection: 220 nM Step 7: benzyl 3,6-diazabicyclo[3.2.1]octane-3-carboxylate hydrochloride (Intermediate A6)

HCl gas was bubbled at a steady rate through a solution of A5 (peak 2) (2.5 g, 7.2 mmol) in EtOAc (36 mL) for 3 min. The solution became warm to the touch and slightly cloudy. The reaction was stirred for another 15 min at room temperature at which point LCMS analysis showed consumption of the starting material. The reaction was purged with $N_2$ for 10 min and concentrated in vacuo to provide Intermediate A6 as a solid. MS (ESI) m/z: 247.2 (M+H).

Intermediate B 2-(1-Cyanocyclopropyl)benzoic Acid

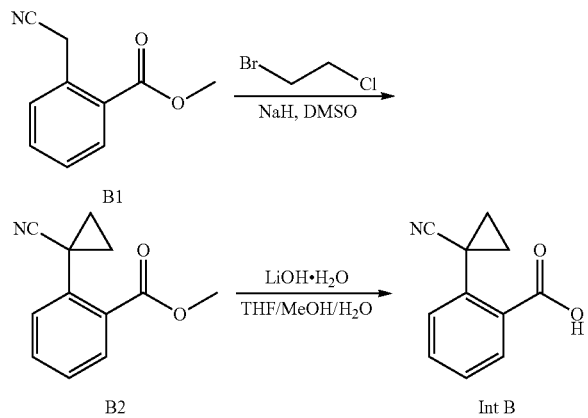

Step 1: Methyl 2-(1-cyanocyclopropyl)benzoate (A2)

To a solution of NaH (1.1 g, 26.2 mmol) in DMSO (20 mL) was added compound B1 (2 g, 11.4 mmol). After stirring at room temperature under nitrogen for 1 h, 1-bromo-2-chloroethane (1.8 g, 12.6 mmol) was added and the mixture stirred at room temperature for 2 h. The mixture was quenched with ice water (10 mL) and extracted with EtOAc (3×10 mL). The organic layer was dried over magnesium sulfate and concentrated in vacuo to give the crude compound, which was purified by column chromatography on silica gel eluting with (petroleum ether/EtOAc 20:1) to give the title compound as a solid.

Step 2: 2-(1-Cyanocyclopropyl)benzoic acid (Intermediate B)

A solution of compound B2 in THF/MeOH/H$_2$O (3:1:1, 16 mL) was treated with lithium hydroxide in water (3 mL). The mixture was stirred overnight at room temperature. The THF and MeOH were removed in vacuo and the resulting solution acidified to pH ~1 with HCl (1 N) to give a crystalline precipitate. The crystals were isolated by filtration, washed with water and dried in vacuo affording Intermediate B as a solid. MS (ESI) m/z: 187.9 (M+H).

Intermediate C 2-(2H-Tetrazol-2-yl)benzoic Acid

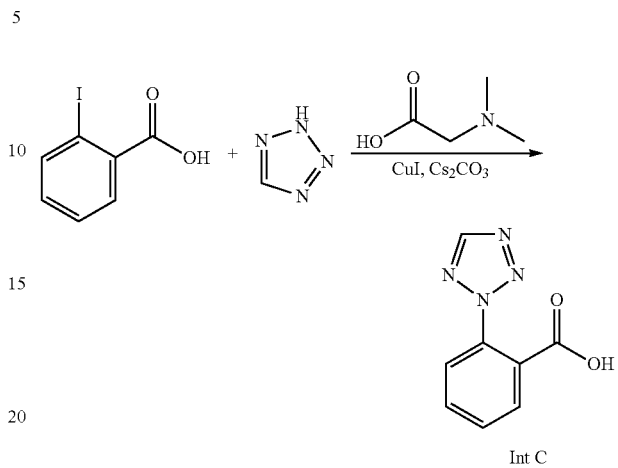

A 20 mL microwave tube was charged with 2-iodobenzoic acid (1.8 g, 7.5 mmol), cesium carbonate (4.1 g, 12.5 mmol), copper(I) iodide (0.13 g, 0.67 mmol), and DMA (8.0 mL). N,N'-Dimethylglycine (0.13 g, 1.3 mmol) and tetrazole (1.3 g, 18.4 mmol) were added, and the solution was heated in a microwave reactor at 100° C. for 1 h. The reaction was diluted with water and 1 N aqeous sodium hydroxide and washed with EtOAc. The aqueous fraction was acidified with conc. HCl and extracted 2× with EtOAc. The combined organic fractions were washed with brine, dried over magnesium sulfate, filtered, and concentrated. The residue was purified by silica gel gradient chromatography [0-85% (1% acetic acid in EtOAc) in hexanes], providing Intermediate C. $^1$H NMR (400 MHz, CD$_3$OD): δ 7.72-7.84 (m, 3 H), 8.07 (dd, J=7.6, 1.6 Hz, 1 H), 8.90 (s, 1 H) ppm. MS (ESI) m/z: 191.2 (M+H).

Intermediate D 3-(1H-Pyrazol-1-yl)pyrazine-2-carboxylic Acid

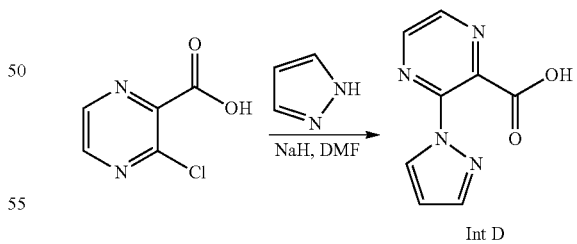

To a suspension of sodium hydride (278 mg, 6.95 mmol, 60% in oil) in DMF (10 mL) was added 1H-pyrazole (279 mg, 4.11 mmol) and the resulting mixture stirred at room temperature for 30 mins. 3-Chloropyrazine-2-carboxylic acid (500 mg, 3.16 mmol) was added and the mixture was heated to 60° C. for 2 h. After cooling to room temperature, water (20 mL) was added and the mixture extracted with 5% MeOH in DCM (3×20 mL). The combined organic layers were washed with brine, dried over Na$_2$SO$_4$, filtered and concentrated in vacuo to give Intermediate D as a solid. LRMS m/z (M+H) 191.0 found, 191.0 required.

Intermediate E 2-(2,2-Difluoroethoxy)nicotinic Acid

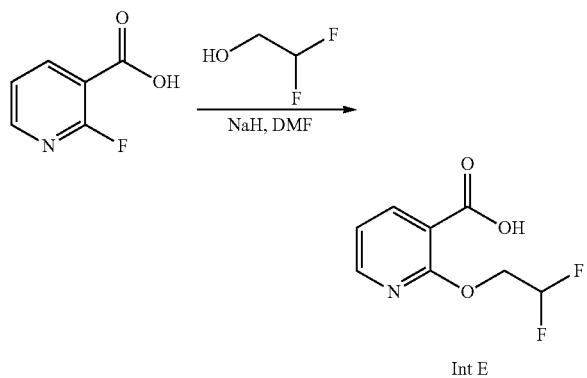

To a suspension of 2,2-difluoroethanol (492 mg, 6.0 mmol) in DMF (10 mL) at 0° C. was added NaH (180 mg, 4.5 mmol), and the mixture stirred at 0° C. for 0.5 h. A suspension of 2-fluoronicotinic acid (423 mg, 3.0 mmol) and NaH (180 mg, 4.5 mmol) in DMF (5 mL) was added dropwise at 0° C. and the resulting mixture stirred at room temperature overnight. The mixture was diluted with water, acidified to pH~3 with 1M HCl and extracted with EtOAc (3×50 mL). The combined organic layers were washed with brine, dried over $MgSO_4$, filtered, and concentrated in vacuo to give the crude product Intermediate E which was used directly without any further purification. LRMS m/z (M+H) 204.1 found, 204.0 required.

Intermediate F 2-(2-Methoxyethyl)benzoic Acid

Step 1: (E)-Methyl 2-(2-methoxyvinyl)benzoate (F1)

To a suspension of (methoxymethyl)triphenylphosphonium bromide (9.44 g, 27.4 mmol) in THF (50 mL) was added NaH (1.46 g, 36.6 mmol) at 0° C. portion wise. The mixture was stirred at 0° C. for 0.5 h and then a solution of methyl 2-formylbenzoate (3.0 g, 18.3 mmol) in THF (15 mL) added dropwise and the reaction mixture stirred at room temperature for 12 h. The mixture was diluted with water, extracted with EtOAc (30 mL×2) and the combined organic layers washed with brine, dried over $MgSO_4$, filtered, and concentrated in vacuo. The residue was purified by silica gel chromatography (petroleum ether/EtOAc=10:1 to 3:1) to give F1 as an oil.

Step 2: Methyl 2-(2-methoxyethyl)benzoate (F2)

To a solution of F1 (2.3 g, 12 mmol) in EtOAc (30 mL) was added Pd/C (200 mg) and the mixture was stirred at room temperature overnight under a balloon of $H_2$. The mixture was filtered through Celite and the filtrate concentrated in vacuo to give F2, which was used directly in the next step.

Step 3: 2-(2-Methoxyethyl)benzoic Acid (Intermediate F)

A mixture of F2 (2.2 g, 11.3 mmol) and LiOH (1.4 g, 34 mmol) in methanol (15 mL) and water (15 mL) was stirred at room temperature overnight. The mixture was adjusted to ~pH 3 with 1N HCl and concentrated in vacuo. The residue was extracted with EtOAc (30 mL×3), and the combined organic layers were dried over $Na_2SO_4$, filtered and the filtrate was concentrated in vacuo to give Intermediate F as a solid that was used without further purification.

Intermediate G 2-(2,2-difluoroethoxy)benzoic Acid

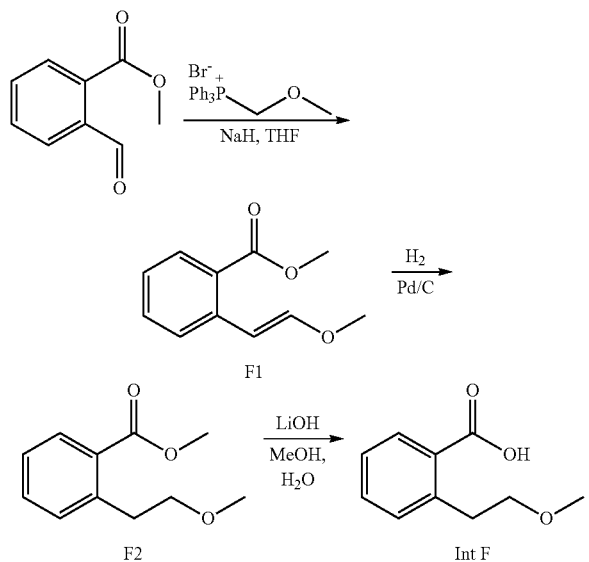

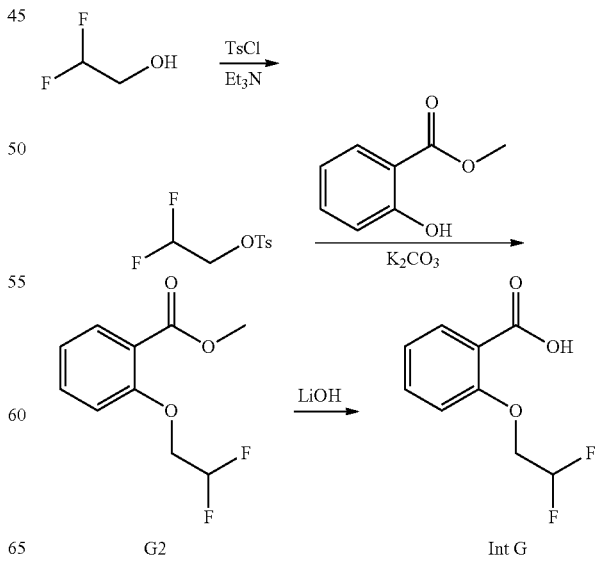

Step 1: 2,2-difluoroethyl 4-methylbenzenesulfonate (G1)

To a solution of compound 2,2-difluoroethanol (8.2 g, 100 mmol) in DCM (200 mL) at 0° C. was added Et₃N (15.1 g, 150 mmol) and TsCl (19.0 g, 100 mmol). The resulting mixture was stirred at 0° C. for 0.5 h, then poured into water and extracted with DCM (3×200 mL). The combined organic layer was dried over MgSO₄, filtered and concentrated in vacuo to give G1 as an oil that was used without further purification. ¹H-NMR (Methanol-d4, 400 MHz): δ 7.74 (d, J=8.2 Hz, 2H), 7.31 (d, J=8.2 Hz, 2H), 5.65-6.07 (m, 1H), 4.10 (td, J=12.6, 4.1 Hz, 2H), 2.40 (s, 3H).

Step 2: methyl 2-(2,2-difluoroethoxy)benzoate (G2)

To a suspension of G1 (7.6 g, 50.0 mmol) and K₂CO₃ (13.8 g, 100 mmol) in THF (300 mL) was added methyl 2-hydroxybenzoate (11.8 g, 50.0 mmol). The resulting mixture was stirred at 70° C. overnight. After cooling to room temperature, the mixture was poured into water and extracted with EtOAc (3×200 mL). The combined organic layer was dried over MgSO4, filtered and concentrated in vacuo. The residue was purified by silica gel chromatography (3% EtOAc in petroleum ether) to give G2 as a solid. ¹H NMR (CDCl₃, 400 MHz): δ 7.73-7.89 (m, 1H), 7.41-7.60 (m, 1H), 7.07 (t, J=7.4 Hz, 1H), 6.96 (d, J=8.2 Hz, 1H), 5.87-6.33 (m, 1H), 4.24 (td, J=12.9, 3.9 Hz, 2H), 3.88 (s, 3H)

Step 3: 2-(2,2-difluoroethoxy)benzoic Acid

To a solution of G2 (4.5 g, 20.8 mmol) in methanol/water (100 mL/100 mL) was added LiOH.H2O (4.37 g, 104 mmol) and the mixture was stirred at room temperature overnight. The mixture was diluted with water (100 mL) and extracted with EtOAc (3×100 mL). The aqueous layer was acidified with HCl (2M) to pH~2 and extracted with DCM (4×100 mL). The combined organic layers were washed with brine, dried over sodium sulfate, filtered and the filtrate was concentrated in vacuo to give Intermediate G as a solid. LRMS m/z (M+H) 203.1 found, 203.1 required. ¹H-NMR (Methanol-d4, 400 MHz): δ 7.80 (dd, J=7.5, 1.5 Hz, 1H), 7.44-7.62 (m, 1H), 7.03-7.28 (m, 2H), 5.97-6.45 (m, 1H), 4.31 (td, J=13.4, 4.0 Hz, 2H).

Intermediate H

2-(2,2-difluorocyclopropyl)benzoic Acid

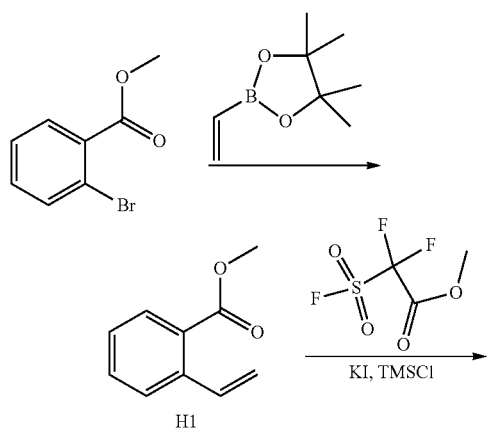

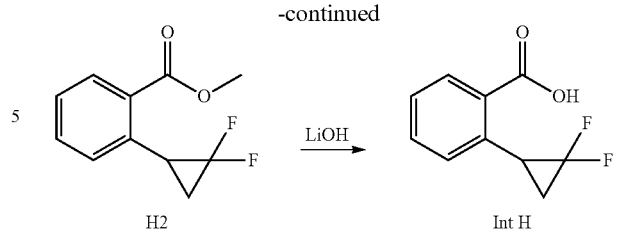

Step 1: methyl 2-vinylbenzoate (H1)

To a solution of methyl 2-bromobenzoate (1.2 g, 5.5 mmol) in dioxane/water (15 mL/0.6 mL) were added 4,4,5,5-tetramethyl-2-vinyl-1,3,2-dioxaborolane (1.7 g, 11.1 mmol), K₂CO₃ (1.53 g, 11.1 mmol) and Pd(dppf)Cl₂ (0.4 g). The resulting mixture was stirred at 100° C. overnight. After cooling to room temperature, the mixture was diluted with water (20 mL) and extracted with EtOAc (3×30 mL). The combined organic layers were washed with brine, dried over sodium sulfate, filtered and the filtrate was concentrated in vacuo. The residue was purified by prep-TLC (10% EtOAc in petroleum ether) to give H1 as an oil. LRMS m/z (M+H) 163.1 found, 163.1 required. ¹H-NMR (Methanol-d4, 400 MHz): δ 7.87 (d, J=7.6 Hz, 1H), 7.28-7.57 (m, 4H), 5.61 (d, J=17.6 Hz, 1H), 5.35 (d, J=11.2 Hz, 1H), 3.88 (s, 3H).

Step 2: methyl 2-(2,2-difluorocyclopropyl)benzoate (H2)

A mixture of H1 (500 mg, 3.09 mmol) and KI (1.15 g, 6.9 mmol) in DME (27.8 mg, 0.31 mmol) and dioxane (461.7 mg, 5.3 mmol) was stirred at 120° C. for 5 min, then TMSCl (667 mg, 6.17 mmol) and methyl 2,2-difluoro-2-(fluorosulfonyl)acetate (1.2 g, 6.2 mmol) were added. The resulting mixture continued to heat for 24 h at which time LC-MS indicated the starting material was converted to the product. After cooling to room temperature, the mixture was quenched with water and extracted with EtOAc (3×10 mL). The combined organic layers were dried over sodium sulfate, filtered and concentrated in vacuo. The residue was purified through Prep-HPLC to afford H2 as a solid. LRMS m/z (M+H) 213.2 found, 213.2 required.

Step 3: 2-(2,2-difluorocyclopropyl)benzoic Acid

A solution of H2 (170 mg, 0.8 mmol) and LiOH (23 mg, 0.55 mmol) in mixed solvent THF:H2O:MeOH (2:2:1) was stirred at 0° C. overnight. The reaction mixture was diluted with H₂O (6 mL), adjusted to pH=2 with 1 M HCl and extracted with EtOAc (3×8 mL). The combined organic layers were washed with brine (10 mL), dried over sodium sulfate, filtered and concentrated in vacuo. The residue was purified by Prep-HPLC to give Intermediate H as a solid. LRMS m/z (M+H) 199.1 found, 199.1 required. ¹H-NMR (Methanol-d4, 400 MHz): δ 7.95 (d, J=7.2 Hz, 1H), 7.34-7.53 (m, 3H), 3.31-3.36 (m, 1H), 1.81-1.84 (m, 1H), 1.62-1.66 (m, 1H).

Intermediate I

2-(2,2-trifluoroethyl)benzoic Acid

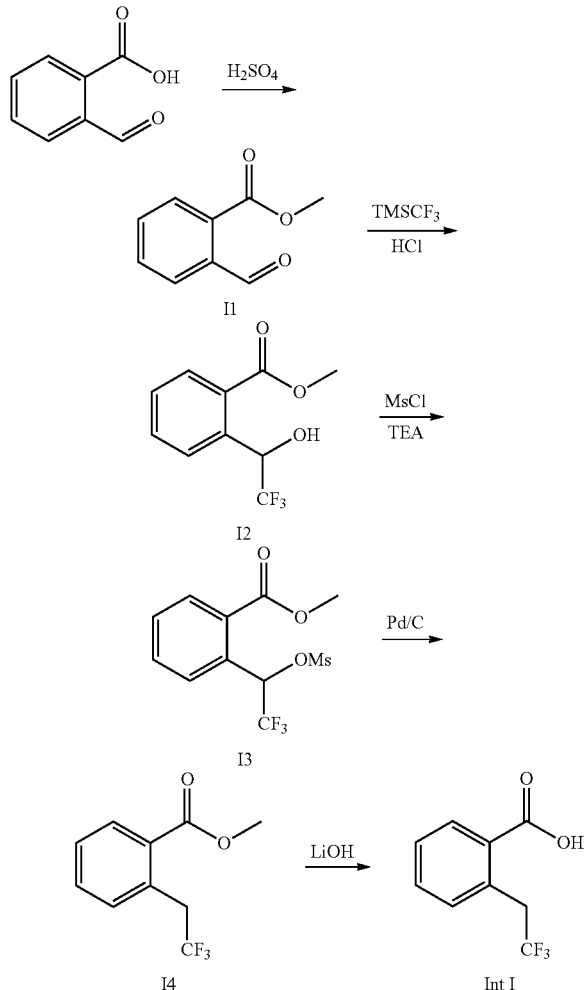

Step 1: methyl 2-formylbenzoate (I1)

To a solution of H$_2$SO$_4$ (2 mL) in MeOH (100 mL) was added 2-formyl benzoic acid (10.0 g, 66.2 mmol). The resulting mixture was stirred at 70° C. overnight. After cooling to room temperature, the mixture was concentrated in vacuo, adjusted to pH~8 with aq. NaHCO$_3$ and extracted with EtOAc (3×10 mL). The combined organic layers were dried over sodium sulfate, filtered and concentrated in vacuo. The residue was purified by silica gel chromatography (10% EtOAc in petroleum ether) to give I1 as an oil. LRMS m/z (M+H) 165.1 found, 165.1 required. $^1$H-NMR (CDCl$_3$, 400 MHz): δ 10.58 (s, 1H), 7.89-7.95 (m, 2H), 7.60-7.63 (m, 2H), 3.95 (s, 3H).

Step 2: methyl 2-(2,2,2-trifluoro-1-hydroxyethyl)benzoate (I2)

To a suspension of I1 (3.60 g, 21.9 mmol) and CsF (1.67 g, 10.9 mmol) in dry THF (36 mL) at 0° C. was added TMSCF$_3$ (4.68 g, 32.9 mmol). The mixture was stirred at 0° C. for 1 h. The mixture was adjusted to pH~2 with 1N HCl solution and stirred for another 1 h and extracted with EtOAc (3×10 mL). The combined organic layer was dried over sodium sulfate, filtered and concentrated in vacuo and the residue was purified by silica gel chromatography (10% EtOAc in petroleum ether) to give I2 as an oil. LRMS m/z (M+H) 235.1 found, 235.1 required. $^1$H-NMR (CDCl$_3$, 400 MHz): δ 7.97 (d, J=8.0 Hz, 1H), 7.69 (d, J=8.0 Hz, 1H), 7.58 (t, J=7.2 Hz, 1H), 7.45 (t, J=7.2 Hz, 1H), 5.92 (br, 1H), 4.51 (br, 1H), 3.92 (s, 3H).

Step 3: methyl 2-(2,2,2-trifluoro-1-((methylsulfonyl)oxy)ethyl)benzoate (I3)

To a solution of I2 (1.10 g, 4.70 mmol) and TEA (1.96 mL, 14.1 mmol) in DCM (10 mL) at room temperature was added MsCl (807 mg, 7.05 mmol) dropwise. The resulting mixture was stirred at room temperature for 1.5 h, diluted with DCM and washed with brine (2×5 mL), dried over anhydrous sodium sulfate, filtered and concentrated in vacuo to give I3 as a solid. LRMS m/z (M+H) 313.0 found, 313.0 required. $^1$H-NMR (CDCl$_3$, 400 MHz): δ 8.07 (d, J=7.6 Hz, 1H), 7.79 (d, J=8.4 Hz, 1H), 7.65 (t, J=6.0 Hz, 1H), 7.51-7.55 (m, 2H), 3.93 (s, 3H), 3.05 (s, 3H).

Step 4: methyl 2-(2,2,2-trifluoroethyl)benzoate (I4)

A solution of I3 (1.00 g, 3.20 mmol) in methanol (40 mL) was stirred in the presence of Pd/C (1.0 g) under 50 psi of H$_2$ atmosphere at 50° C. overnight. LCMS indicated the reaction was completed and the mixture was filtered through a pad of Celite. The filtrate was concentrated in vacuo to give I4 as an oil. LRMS m/z (M+H) 219.1 found, 219.1 required.

Step 5: 2-(2,2,2-trifluoroethyl)benzoic Acid

To a solution of I4 (550 mg, 2.50 mmol) in MeOH/H$_2$O (10 mL/1 mL) was added LiOH (240 mg, 10.0 mmol) and the resulting mixture was stirred at room temperature for 12 h. Water (10 mL) was added and the mixture was washed with EtOAc (2×10 mL) and adjusted to pH ~3 with conc HCl and extracted with DCM (3×20 mL). The combined organic layer was washed with brine (20 mL), dried over sodium sulfate, filtered and concentrated in vacuo to give Intermediate I as a solid. LRMS m/z (M+H) 205.0 found, 205.0 required. $^1$H-NMR (Methanol-d4, 400 MHz): δ 7.99 (d, J=7.4 Hz, 1H), 7.49-7.58 (m, 1H), 7.37-7.49 (m, 2H), 4.09 (q, J=11.0 Hz, 2H)

Intermediate J

2-(2,2-difluoroethyl)benzoic Acid

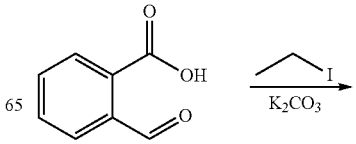

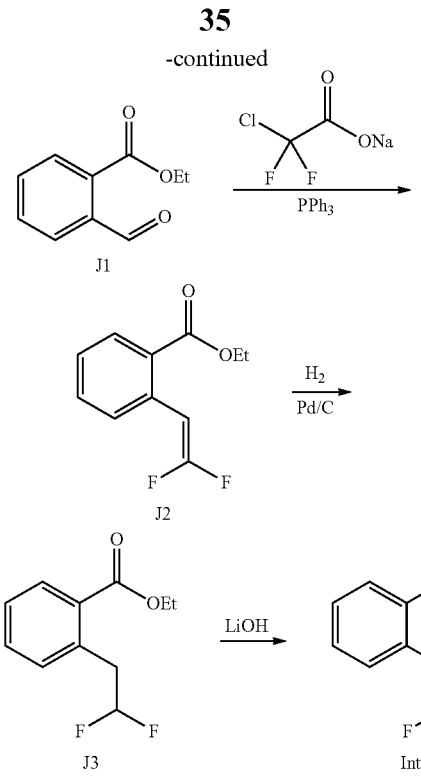

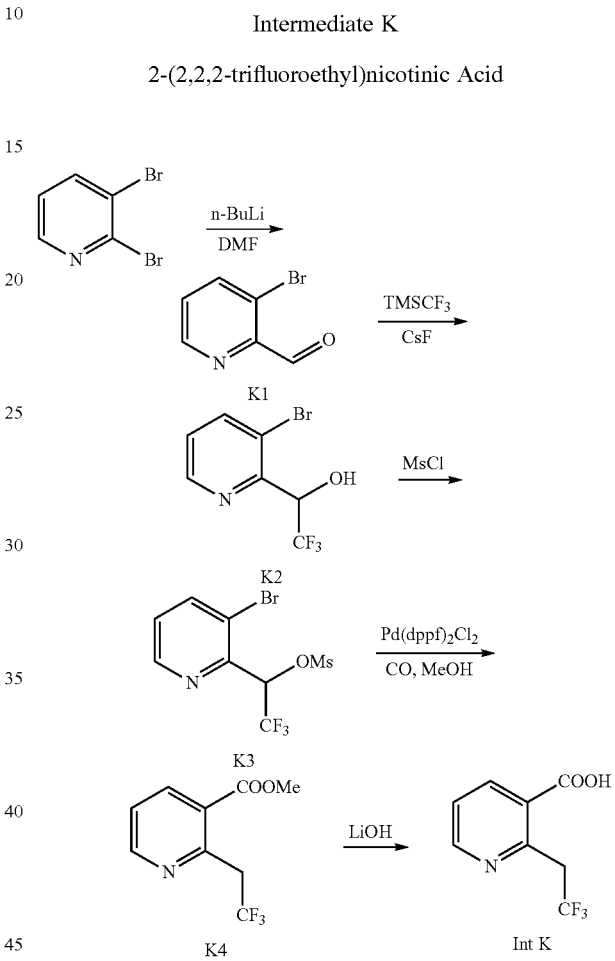

Step 1: ethyl 2-formylbenzoate (J1)

To a suspension of 2-formylbenzoic acid (34.5 g, 0.23 mol) and $K_2CO_3$ (65.1 g, 0.47 mol) in acetone (500 mL) was added EtI (72 g, 0.46 mol). The resulting mixture was stirred at 70° C. overnight. After cooling to room temperature, the mixture was filtered and the filtrate was concentrated in vacuo to give J1 as an oil which was used without further purification. LRMS m/z (M+H) 179.2 found, 179.2 required.

Step 2: ethyl 2-(2,2-difluorovinyl)benzoate (J2)

To a stirred solution of J1 (20.0 g, 0.11 mol) in DMF (190 mL) was added $F_2ClCCO_2Na$ (25.6 g, 0.17 mol) and $PPh_3$ (44.2 g, 0.17 mol). The resulting mixture was stirred at 120° C. overnight. After cooling to room temperature, the mixture was diluted with water (200 mL) and extracted with EtOAc (2×300 mL). The combined organic layer was washed with brine (2×300 mL), dried over $Na_2SO_4$, filtered and concentrated in vacuo. The crude residue was purified by silica gel chromatography (0-10% EtOAc in petroleum ether) to give J2 as an oil along with the crude product that contained triphenylphosphine oxide. LRMS m/z (M+H) 213.2 found, 213.2 required.

Step 3: ethyl 2-(2,2-difluoroethyl)benzoate (J3)

To a stirred solution of J2 (2.7 g, 13 mmol) in EtOH (80 mL) was added Pd/C (0.4 g). The resulting mixture was stirred at 50° C. under hydrogen atmosphere (50 psi) overnight. After cooling to room temperature, the mixture was filtered and the filtrate was concentrated in vacuo to give J3 as an oil. LRMS m/z (M+H) 215.2 found, 215.2 required.

Step 4: 2-(2,2-difluoroethyl)benzoic Acid

To a solution of J3 (2.7 g, 12.6 mmol) in $THF/H_2O$ (20 mL/7 mL) was added $LiOH.H_2O$ (1.06 g, 25.2 mmol) and the resulting mixture was stirred at room temperature overnight. The solvent was removed in vacuo, the residue was diluted with water (20 mL) and extracted with EtOAc (3×20 mL). The aqueous layer was adjusted to Ph~3 and the precipitated solid was collected via filtration to give Intermediate J as a solid. $^1$H-NMR (Methanol-d4, 400 MHz): δ 3.56 (td, J=16.63, 4.64 Hz, 2 H), 5.87-6.30 (m, 1 H), 7.35-7.46 (m, 2 H), 7.49-7.59 (m, 1 H), 8.02 (d, J=7.78 Hz, 1 H).

Intermediate K 2-(2,2,2-trifluoroethyl)nicotinic Acid

Step 1: 2-(2,2-difluoroethyl)benzoic Acid (K1)

To a solution of 2,3-dibromopyridine (10 g, 42.2 mmol) in toluene (100 mL) was dropwise added nBuLi (20.26 mL, 50.7 mmol) at −78° C. under $N_2$. After the resulting mixture was stirred at −78° C. for 2 h, DMF (3.92 mL, 50.7 mmol) was added dropwise and the mixture was stirred at −78° C. for another 2 h. TLC analysis of the reaction mixture (50% EtOAc in petroleum ether) indicated the reaction was finished. The mixture was quenched with water at −78° C. and extracted with EtOAc (3×300 mL). The combined organic layers were dried over $MgSO_4$, filtered and concentrated in vacuo. The residue was purified by silica gel chromatography (25% EtOAc in petroleum ether) to give K1 as an oil. LRMS m/z (M+H) 186.1 found, 186.1 required.

Step 2: 2-(2,2-difluoroethyl)benzoic Acid (K2)

To a suspension of K1 (3.5 g, 18.9 mmol) and CsF (4.3 g, 28.4 mmol) in THF (30 mL) at 0° C. was added $TMSCF_3$ (4.0 g, 28.4 mmol) under $N_2$. The resulting mixture was stirred at room temperature for 2 h. The mixture was diluted with water and extracted with EtOAc (3×100 mL). The organic layers were combined and dried over $MgSO_4$, filtered and concentrated in vacuo. The crude residue was purified by silica gel chromatography (25% EtOAc in petroleum ether) to give K2 as an oil. LRMS m/z (M+H) 256.1 found, 256.1 required.

Step 3: 2-(2,2-difluoroethyl)benzoic acid (K3)

To a solution of K2 (1.8 g, 7 mmol) and DIPEA (1.8 g, 14 mmol) in DCM (10 mL) was added MsCl (1.1 mL, 14 mmol) dropwise at 0° C. under $N_2$ and the mixture was stirred at 0° C. for 2 h. The mixture was diluted with water, extracted with EtOAc (3×200 ml) and the organic layers were combined, dried over MgSO4, filtered and concentrated in vacuo to give K3 as an oil that was used without further purification. LRMS m/z (M+H) 334.3 found, 334.3 required.

Step 4: 2-(2,2-difluoroethyl)benzoic Acid (K4)

A mixture of K3 (1.0 g, 3 mmol), Pd(dppf)Cl$_2$ (100 mg), and triethylamine (909 mg, 9 mmol) in methanol (30 mL) was stirred at 120° C. for 16 h under CO (3 MPa) atmosphere. The reaction was cooled to room temperature, filtered, and concentrated in vacuo. The crude residue was purified by silica gel chromatography (25% EtOAc in petroleum ether) to give K4 as an oil. LRMS m/z (M+H) 220.1 found, 220.1 required.

Step 5: 2-(2,2-difluoroethyl)benzoic Acid

To a solution of K4 (1.0 g, 4.6 mmol) in MeOH (15 ml) and water (15 mL) was added LiOH (0.22 g, 9.1 mmol) and the mixture was stirred at room temperature for 2 h. The MeOH was removed under reduced pressure and the crude residue was diluted with water (20 mL) and extracted with EtOAc (3×100 mL). The aqueous layer was adjusted to pH~2 with conc. HCl and then extracted with EtOAc (3×100 ml). The organic layers were combined, dried over $MgSO_4$, filtered and concentrated in vacuo to give Intermediate K as a solid. LRMS m/z (M+H) 206.1 found, 206.1 required. $^1$H-NMR (Methanol-d4, 400 MHz): δ 8.30-8.70(m, 2H), 7.30-7.60 (m, 1H) 4.00-4.50 (m, 2H).

Intermediate L 2-propylbenzoic Acid

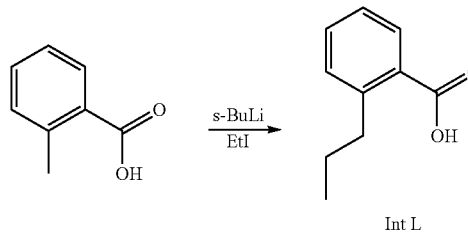

2-propylbenzoic Acid

To a solution of 2-methylbenzoic acid (20 g, 0.15 mmol) in THF (200 mL) was added s-BuLi (340 mL, 0.45 mmol)

dropwise at −78° C. After addition, the mixture was stirred at −78° C. for 0.5 h and iodoethane (137 g, 0.88 mmol) was added. The mixture was allowed to warm to room temperature and was stirred overnight, quenched with water and extracted with EtOAc (3×300 mL). The combined organic layers were washed with brine, dried over $MgSO_4$, filtered and concentrated in vacuo . The residue was purified by silica gel chromatography (50% EtOAc in petroleum ether) to give Intermediate L as an oil. LRMS m/z (M+H) 165.1 found, 165.1 required. $^1$H-NMR (DMSO-d6, 400 MHz): δ 12.80 (brs, 1 H), 7.75~7.73 (m, 1 H), 7.39~7.43 (m, 1 H), 7.22~7.36 (m, 2 H), 2.87~2.84 (m, 2 H), 1.49~1.54 (m, 2 H), 0.84~0.87 (m, 3 H).

Intermediate M 2-cyclopropyl-4-fluorobenzoic Acid

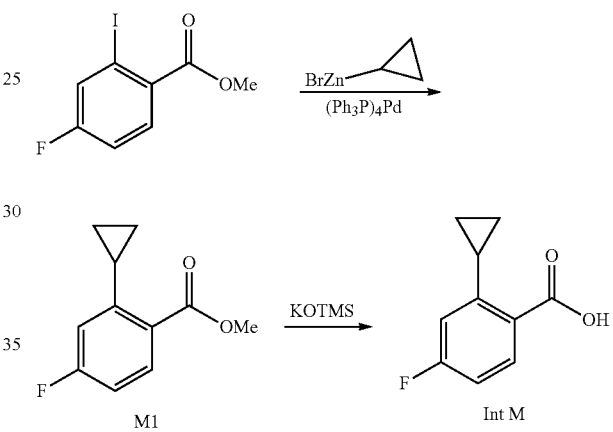

Step 1: methyl 2-cyclopropyl-4-fluorobenzoate (M1)

To a solution of methyl 4-fluoro-2-iodobenzoate (1.0 g, 3.6 mmol) in THF (24 mL) was added cyclopropyl zinc bromide (17.8 mL, 8.9 mmol, 0.5 M solution in THF) and tetrakis(triphenylphosphine)palladium(0). After stirring at 100° C. for 4 h, the reaction was cooled to room temperature, diluted with EtOAc and water and filtered through Celite. The organic layer was dried over $MgSO_4$, filtered and concentrated, and the crude material was purified by silica gel chromatography (0-10% EtOAc in hexanes) to give M1 as an oil. MS (ESI) m/z: 195.3 (M+H).

Step 2: 2-cyclopropyl-4-fluorobenzoic Acid

To a solution of M1 (650 mg, 3.4 mmol) in THF (10 mL) was added potassium trimethylsilanolate (644 mg, 5.0 mmol) and the reaction was stirred overnight at room temperature. The precipitated solids were collected by filtration and rinsed with diethyl ether. The solid was further dried under high vacuum to provide Intermediate M as the potassium salt that was used without further purification. MS (ESI) m/z: 181.2 (M+H).

Intermediate N

2-(2H-1,2,3-triazol-2-yl)benzoic Acid

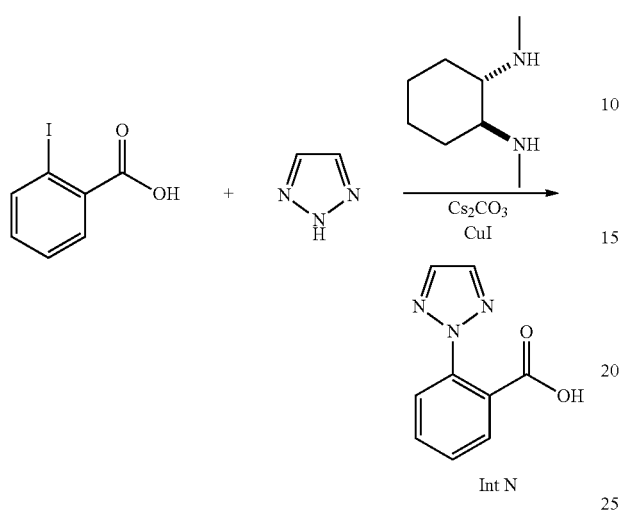

Int N

2-(2H-1,2,3-triazol-2-yl)benzoic Acid

To a solution of 2-iodobenzoic acid (3.0 g, 12.1 mmol) in DMF was added 1,2,3-triazole (1.5 g, 21.7 mmol), Cs$_2$CO$_3$ (7.1 g, 21.7 mmol), CuI (114 mg, 0.6 mmol), and trans-N,N'-dimethylcyclohexane-1,2-diamine (310 mg, 2.2 mmol). After heating at 120° C. for 10 min in a microwave reactor, the mixture was cooled to room temperature, diluted with EtOAc, and filtered through Celite. The filtrate was concentrated in vacuo and the crude residue was purified by silica gel chromatography (MeOH in DCM with 0.1% AcOH) to give Intermediate N as the faster eluting isomer. $^1$H NMR (DMSO-d6, 500 MHz) δ 13.05 (brs, 1 H), 8.12 (s, 2H), 7.81-7.52 (m, 4H).

Example 1

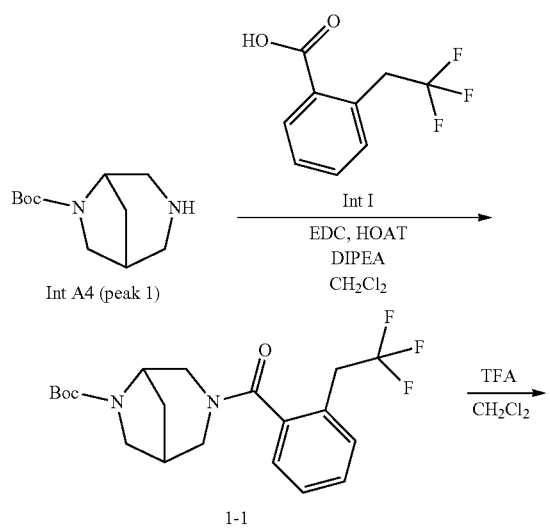

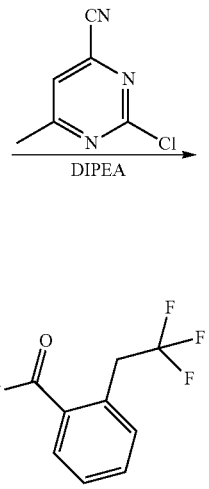

6-methyl-2-(3-(2-(2,2,2-trifluoroethyl)benzoyl)-3,6-diazabicyclo[3.2.1]octan-6-yl)pyrimidine-4-carbonitrile

Step 1: tert-butyl 3-(2-(2,2,2-trifluoroethyl)benzoyl)-3,6-diazabicyclo[3.2.1]octane-6-carboxylate (1-1)

A slurry of tert-butyl 3,6-diazabicyclo[3.2.1]octane-6-carboxylate Intermediate A4 (peak 1) (50 mg, 0.24 mmol), 2-(2,2,2-trifluoroethyl)benzoic acid (96 mg, 0.47 mmol), EDC (54.2 mg, 0.28 mmol), HOAT (38.5 mg, 0.28 mmol, 1.2 eq) and diisopropylethylamine (0.206 ml, 1.18 mmol) in dichloromethane (1 mL) was stirred overnight at room temperature. The reaction mixture was diluted with dichloromethane (20 mL) and washed with saturated aqueous sodium bicarbonate solution (20 mL). The organic layer was separated, dried over sodium sulfate, filtered and concentrated in vacuo to give 1-1 as an oil that was carried forward to the next step without purification. LRMS m/z (M+H) 399.4 found, 399.2 required.

Step 2: 3,6-diazabicyclo[3.2.1]octan-3-yl(2-(2,2,2-trifluoroethyl)phenyl)methanone (1-2)

A slurry of crude tert-butyl 3-(2-(2,2,2-trifluoroethyl)benzoyl)-3,6-diazabicyclo[3.2.1]octane-6-carboxylate (94 mg, 0.24 mmol, 1) in dichloromethane (2 mL) and TFA (2 mL) was allowed to stir at room temperature for 2 h. The reaction mixture was diluted with toluene (5 mL) and concentrated in vacuo to give 1-2 as an oil that was carried forward to the next step without purification. LRMS m/z (M+H) 298.2 found, 298.1 required.

Step 3: 6-methyl-2-(3-(2-(2,2,2-trifluoroethyl)benzoyl)-3,6-diazabicyclo[3.2.1]octan-6-yl)pyrimidine-4-carbonitrile A solution of crude 3,6-diazabicyclo[3.2.1]octan-3-yl(2-(2,2,2-trifluoroethyl)phenyl)methanone (70 mg, 0.24 mmol, 1-2) and diisopropylethylamine (0.41 mL, 2.4 mmol) in acetonitrile (2 mL) was heated in a sealed vial at 100° C. for 16 h. The reaction mixture was concentrated in vacuo and the crude residue was purified by silica gel chromatography (0-60% EtOAc in hexanes over 16 min) to give the title compound as a foam. LRMS m/z (M+H) 416.3 found, 416.2 required.

TABLE 1

The following compounds were prepared using the foregoing methodology and general procedure described in Example 1, but substituting the appropriate appropriate benzoic acid in Step 1, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 2 | 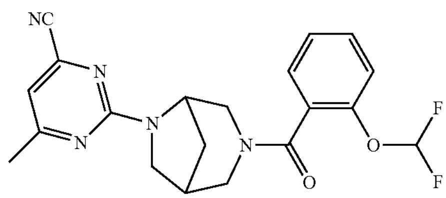 [SMILES: Cc1cc(C#N)nc(N2CC3CC2CN(C(=O)c2ccccc2OC(F)F)C3)n1] | 2-(3-(2-(difluoromethoxy)benzoyl)-3,6-diazabicyclo[3.2.1]-octan-6-yl)-6-methylpyrimidine-4-carbonitrile | 400.3 |
| 3 | 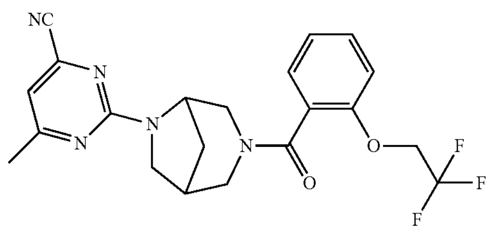 [SMILES: Cc1cc(C#N)nc(N2CC3CC2CN(C(=O)c2ccccc2OCC(F)(F)F)C3)n1] | 6-methyl-2-(3-(2-(2,2,2-trifluoroethoxy)benzoyl)-3,6-diazabicyclo[3.2.1]octan-6-yl)pyrimidine-4-carbonitrile | 432.3 |
| 4 | 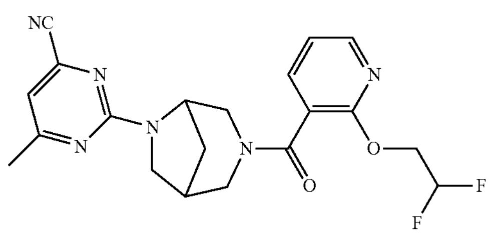 [SMILES: Cc1cc(C#N)nc(N2CC3CC2CN(C(=O)c2cccnc2OCC(F)F)C3)n1] | 2-(3-{[2-(2,2-difluoroethoxy)pyridin-3-yl]carbonyl}-3,6-diazabicyclo[3.2.1]oct-6-yl)-6-methylpyrimidine-4-carbonitrile | 415.4 |
| 5 | 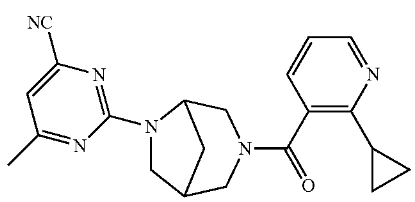 [SMILES: Cc1cc(C#N)nc(N2CC3CC2CN(C(=O)c2cccnc2C2CC2)C3)n1] | 2-(3-(2-cyclopropylnicotinoyl)-3,6-diazabicyclo[3.2.1]octan-6-yl)-6-methylpyrimidine-4-carbonitrile | 375.3 |
| 6 | 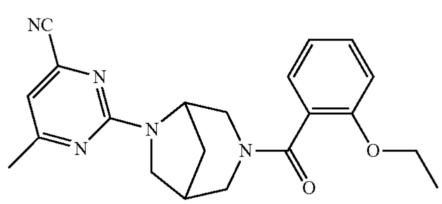 [SMILES: CCOc1ccccc1C(=O)N1CC2CC(C1)N(c1nc(C)cc(C#N)n1)C2] | 2-(3-(2-(methoxymethyl)-benzoyl)-3,6-diazabicyclo-[3.2.1]octan-6-yl)-6-methylpyrimidine-4-carbonitrile | 378.3 |
| 7 | 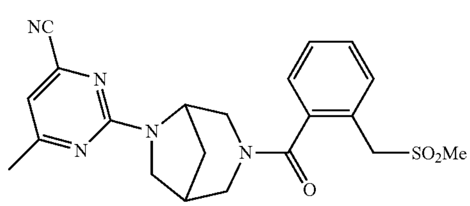 [SMILES: Cc1cc(C#N)nc(N2CC3CC2CN(C(=O)c2ccccc2CS(C)(=O)=O)C3)n1] | 6-methyl-2-(3-(2-((methylsulfonyl)methyl)benzoyl)-3,6-diazabicyclo[3.2.1]octan-6-yl)pyrimidine-4-carbonitrile | 426.3 |

Example 8

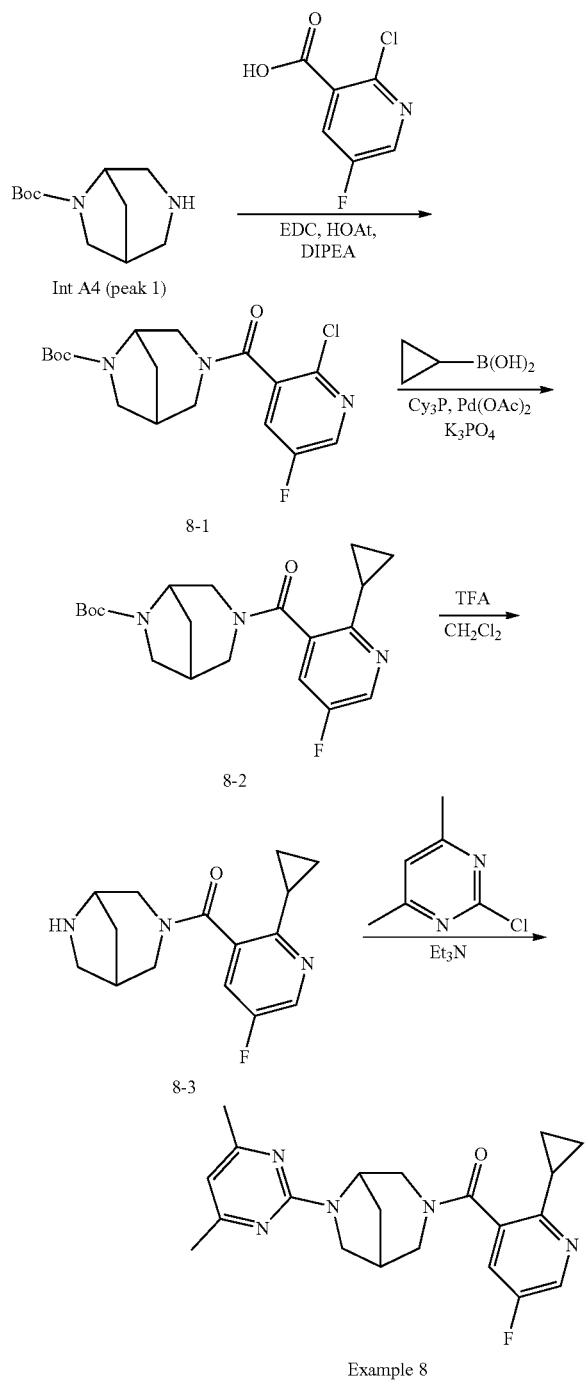

(2-cyclopropyl-5-fluoropyridin-3-yl)(6-(4,6-dimethylpyridin-2-yl)-3,6-diazabicyclo[3.2.1]octan-3-yl)methanone Step 1: tent-butyl 3-(2-chloro-5-fluoronicotinoyl)-3,6-diazabicyclo[3.2.1]octane-6-carboxylate (8-1)

A solution of tent-butyl 3,6-diazabicyclo[3.2.1]octane-6-carboxylate Intermediate A4 (peak 1) (100 mg, 0.47 mmol), 2-chloro-5-fluoronicotinic acid (124 mg, 0.71 mmol), EDC (135 mg, 0.71 mmol), HOAt (96 mg, 0.71 mmol), and N,N-diisopropylethylamine (0.25 ml, 1.41 mmol) in acetonitrile (0.5 mL) was stirred at room temperature for 24 h. The reaction was concentrated in vacuo and the crude residue was purified by silica gel chromatography (0-100% EtOAc/hexanes, 15 minutes) providing 8-1 as an oil. MS (ESI) m/z: 370.3 (M+H).

Step 2: tent-butyl 3-(2-cyclopropyl-5-fluoronicotinoyl)-3,6-diazabicyclo[3.2.1]octane-6-carboxylate (8-2)

A 5 mL microwave tube was charged with tert-butyl 3-(2-chloro-5-fluoronicotinoyl)-3,6-diazabicyclo[3.2.1]octane-6-carboxylate 8-1 (75 mg, 0.20 mmol). Toluene (2 mL) and water (0.5 mL) were added and the solution was degassed under a steam of nitrogen. Cyclopropylboronic acid (26.1 mg, 0.30 mmol), tripotassium phosphate (129 mg, 0.61 mmol), tricyclohexylphosphine (17.1 mg, 0.06 mmol), and palladium(II) acetate (6.8 mg, 0.03 mmol) were added and the sealed tube was heated at 120° C. under microwave radiation for 2 h. The cooled reaction mixture was filtered through a pad of celite and the pad was washed with methanol. The filtrate was concentrated in vacuo to give an orange brown residue that was purified by silica gel chromatography (0-100% EtOAc/hexanes, 20 minutes) to afford 8-2 as an oil. MS(ESI) m/z: 376.4 (M+H).

Step 3: 3,6-diazabicyclo[3.2.1]octan-3-yl (2-cyclopropyl-5-fluoropyridin-3-yl)methanone (8-3)

To a solution of tent-butyl 3-(2-cyclopropyl-5-fluoronicotinoyl)-3,6-diazabicyclo[3.2.1]octane-6-carboxylate 8-2 (54 mg, 0.144 mmol) in CH$_2$Cl$_2$ (1 ml) was added TFA (0.554 ml, 7.19 mmol). The mixture was stirred at room temperature for 1 h and concentrated in vacuo to give 8-3 as an oil. MS(ESI) m/z: 276.3 (M+H).

Step 4: (2-cyclopropyl-5-fluoropyridin-3-yl)(6-(4,6-dimethylpyridin-2-yl)-3,6-diazabicyclo[3.2.1]octan-3-yl)methanone (Example 8)

A mixture of 3,6-diazabicyclo[3.2.1]octan-3-yl(2-cyclopropyl-5-fluoropyridin-3-yl)methanone 8-3 (27 mg, 0.073 mmol), 2-chloro-4,6-dimethylpyrimidine (15.51 mg, 0.109 mmol), and triethylamine (0.051 ml, 0.363 mmol) in acetonitrile (0.5 ml) was stirred in a sealed tube at 85° C. for 72 h. The cooled reaction mixture was purified directly on reversed phase HPLC (sunfire prep C18 OBP 10 µm, 30×150 mm column, 10-70% CH$_3$CN/water with 0.1% TFA, 15 min). The product fractions were combined, neutralized by the addition of saturated NaHCO$_3$ solution, and extracted with EtOAc (3×35 ml). The combined organic extracts were dried over MgSO$_4$ and concentrated in vacuo to give Example 8 as an oil. MS (ESI) m/z: 382.4 (M+H).

Example 9

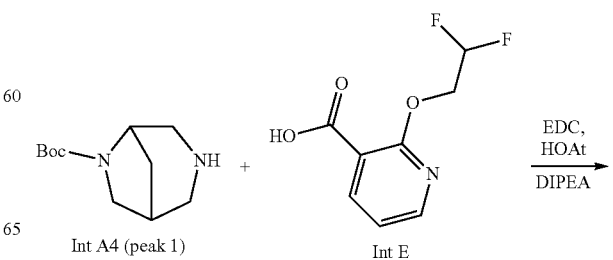

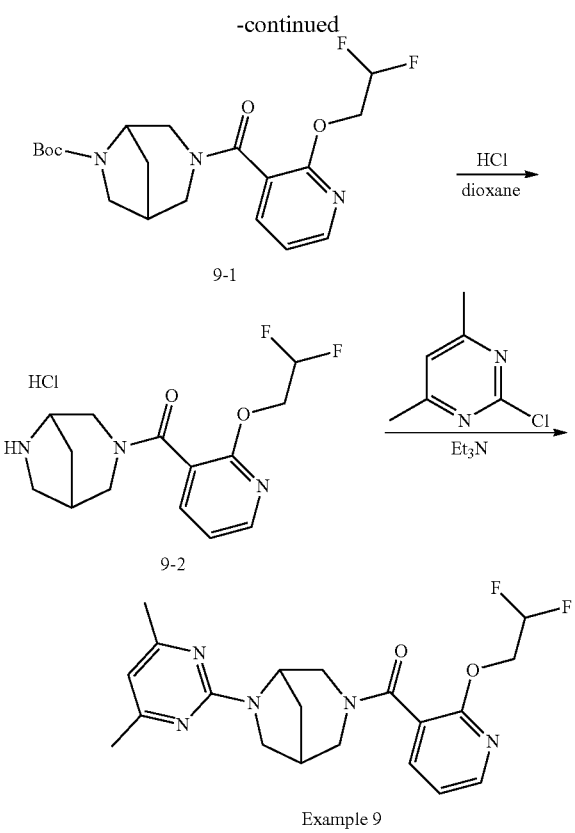

9-1

9-2

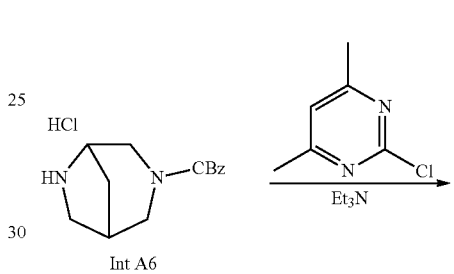

Example 9

(2-(2,2-difluoroethoxy)pyridin-3-yl)(6-(4,6-dimethylpyrimidin-2-yl)-3,6-diazabicyclo[3.2.1]octan-3-yl)methanone Step 1: tert-butyl 3-(2-(2,2-difluoroethoxy)nicotinoyl)-3,6-diazabicyclo[3.2.1]octane-6-carboxylate (9-1)

To a solution of Intermediate A4 (peak 1) (8.0 g, 37.7 mmol), EDC (8.7 g, 45.2 mmol), 1-hydroxy-7-azabenzotriazole (6.2 g, 45.2 mmol), and Intermediate E (8.4 g, 41.5 mmol) in DCM (100 mL) was added diisopropylethylamine (20 mL, 115 mmol) and the mixture was stirred at room temperature overnight. The reaction mixture was washed with saturated aqueous sodium bicarbonate solution (2×100 mL). The organic layer was separated, dried over sodium sulfate, filtered and concentrated in vacuo. The crude material was purified by silica gel chromatography (0-100% EtOAC in hexanes, 25 min) to provide 9-1. MS (ESI) m/z: 398.4 (M+H).

Step 2: 3,6-diazabicyclo[3.2.1]octan-3-yl(2-(2,2-difluoroethoxy)pyridin-3-yl)methanone hydrochloride (9-2)

A solution of 9-1 (12.4 g, 31.2 mmol) in dioxane (250 mL) was cooled in an ice bath and HCl was bubbled in at a constant rate for 15 min. The ice bath was removed and the reaction was stirred for 30 min. The solution was concentrated in vacuo and the crude residue was dissolved in EtOAc, at which point a white solid began to precipitate. The mixture was concentrated again, followed by addition of EtOAc. The slurry was sonicated and then filtered to provide 9-2 as a solid that was used directly in the next step. MS (ESI) m/z: 298.3 (M+H).

Step 3: (2-(2,2-difluoroethoxy)pyridin-3-yl)(6-(4,6-dimethylpyrimidin-2-yl)-3,6-diazabicyclo[3.2.1]octan-3-yl)methanone A solution of 9-2 (9 g, 24.3 mmol), 2-chloro-4,6-dimethylpyrimidine (5.2 g, 36.5 mmol), and Hunig's base (17 mL, 97 mmol) in acetonitrile (100 mL) was heated in a sealed flask at 80° C. for 2 d. After cooling to room temperature, the mixture was concentrated to dryness and the crude material was purified by silica gel chromatography (0-100% EtOAc in hexanes, 25 min) to provide Example 9 as a solid. MS (ESI) m/z: 404.4 (M+H).

Example 10

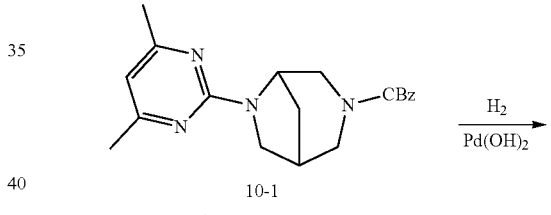

Int A6

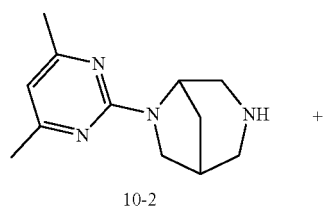

10-1

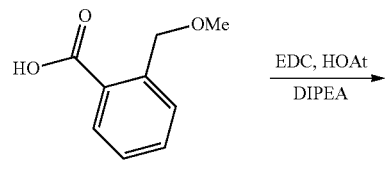

10-2

10-3

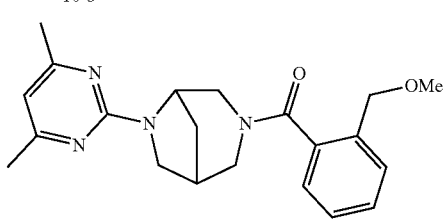

Example 10

(6-(4,6-dimethylpyrimidin-2-yl)-3,6-diazabicyclo[3.2.1]octan-3-yl)(2-(methoxymethyl)phenyl)methanone Step 1: Benzyl 6-(4,6-dimethylpyrimidin-2-yl)-3,6-diazabicyclo[3.2.1]octane-3-carboxylate (10-1)

A mixture of benzyl 3,6-diazabicyclo[3.2.1]octane-3-carboxylate hydrochloride Intermediate A6 (700 mg, 2.5 mmol), 2-chloro-4,6-dimethylpyrimidine (424 mg, 3.0 mmol), and triethylamine (1.7 ml, 12.4 mmol) in acetonitrile (5 ml) was stirred in a sealed tube at 85° C. for 96 h. The cooled mixture was concentrated in vacuo to give an orange semi-solid that was dissolved in a minimal amount of dichloromethane. The triethylamine hydrochloride solid was filtered and the filtrate was purified by silica gel chromatography (0-100% EtOAc/hexanes, 15 minutes) to give 10-1 as an oil. MS (ESI) m/z: 353.4 (M+H).

Step 2: 6-(4,6-dimethylpyrimidin-2-yl)-3,6-diazabicyclo[3.2.1]octane (10-2)

A solution of benzyl 6-(4,6-dimethylpyrimidin-2-yl)-3,6-diazabicyclo[3.2.1]octane-3-carboxylate 10-1 (885 mg, 2.5 mmol) in ethyl acetate (20 ml) was subjected to 2 cycles of the evacuation/backfilling with nitrogen and then treated with Pearlman's catalyst (20 wt %) (176 mg, 0.25 mmol). The evacuation/backfilling with nitrogen procedure was repeated two times and then the nitrogen atmosphere was exchanged for a hydrogen atmosphere by evacuation/backfilling with a balloon of hydrogen. After stirring under a hydrogen atmosphere at room temperature for 2 h, the mixture was filtered through a pad of Celite and the pad was washed with EtOAc (500 mL). The filtrate was concentrated in vacuo to provide 10-2 as a yellow oil that solidified on standing to give a waxy solid that was used without further purification. MS (ESI) m/z: 219.3 (M+H).

Step 3: (6-(4,6-dimethylpyrimidin-2-yl)-3,6-diazabicyclo[3.2.1]octan-3-yl)(2-(methoxymethyl)phenyl)methanone A solution of 6-(4,6-dimethylpyrimidin-2-yl)-3,6-diazabicyclo[3.2.1]octane 10-2 (50 mg, 0.34 mmol), 2-(methoxymethyl)benzoic acid 10-3 (46 mg, 0.28 mmol), EDC (66 mg, 0.34 mmol), HOAt (47 mg, 0.34 mmol), and N,N-diisopropylethylamine (0.12 ml, 0.69 mmol) in acetonitrile (0.5 ml) was stirred at room temperature overnight. The reaction mixture was concentrated in vacuo and the crude residue was purified by silica gel chromatography (0-100% EtOAc in hexanes, 20 min gradient) to give the title compound. MS (ESI) m/z: 367.4 (M+H).

TABLE 2

The following compounds were prepared using the foregoing methodology and general procedure described in Example 10, but substituting the appropriate benzoic acid in Step 3, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 11 | 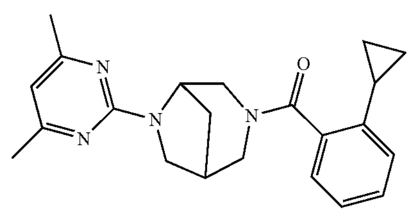 [SMILES: Cc1cc(C)nc(N2CC3CC2CN(C(=O)c2ccccc2C2CC2)C3)n1] | 3-[(2-cyclopropylphenyl)carbonyl]-6-(4,6-dimethylpyrimidin-2-yl)-3,6-diazabicyclo[3.2.1]octane | 363.2 |
| 12 | 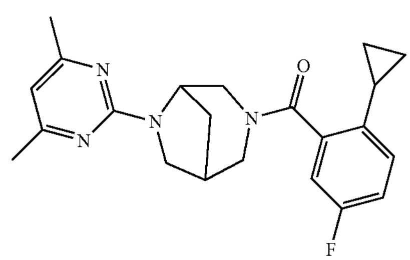 [SMILES: Cc1cc(C)nc(N2CC3CC2CN(C(=O)c2cc(F)ccc2C2CC2)C3)n1] | 3-[(2-cyclopropyl-5-fluorophenyl)carbonyl]-6-(4,6-dimethylpyrimidin-2-yl)-3,6-diazabicyclo[3.2.1]octane | 381.2 |
| 13 | 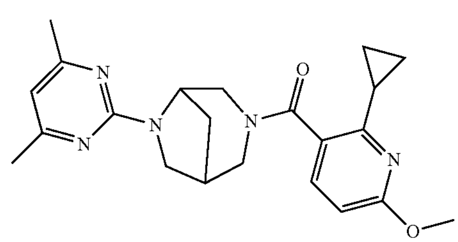 | 3-[(2-cyclopropyl-6-methoxypyridin-3-yl)carbonyl]-6-(4,6-dimethylpyrimidin-2-yl)-3,6-diazabicyclo[3.2.1]octane | 394.2 |

TABLE 2-continued

The following compounds were prepared using the foregoing methodology and general procedure described in Example 10, but substituting the appropriate benzoic acid in Step 3, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 14 | 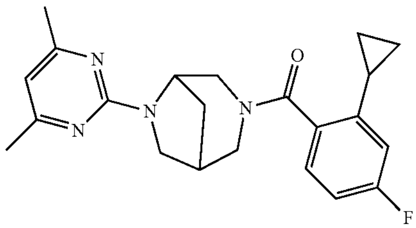 [SMILES: Cc1cc(C)nc(N2CC3CC2CN(C(=O)c2ccc(F)cc2C2CC2)C3)n1] | 3-[(2-cyclopropyl-4-fluorophenyl)carbonyl]-6-(4,6-dimethylpyrimidin-2-yl)-3,6-diazabicyclo[3.2.1]octane | 381.2 |
| 15 | 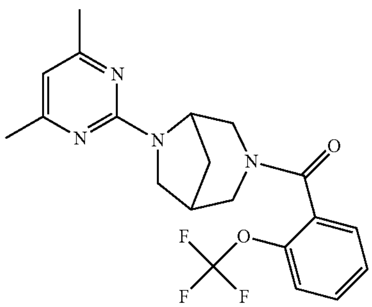 [SMILES: Cc1cc(C)nc(N2CC3CC2CN(C(=O)c2ccccc2OC(F)(F)F)C3)n1] | 6-(4,6-dimethylpyrimidin-2-yl)-3-{[2-(trifluoromethoxy)-phenyl]carbonyl}-3,6-diazabicyclo[3.2.1]octane | 407.2 |
| 16 | 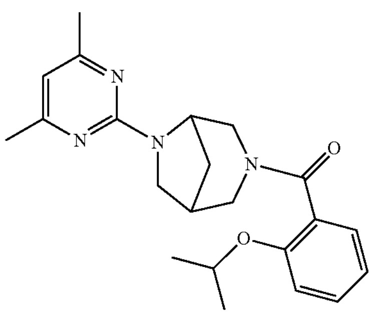 [SMILES: Cc1cc(C)nc(N2CC3CC2CN(C(=O)c2ccccc2OC(C)C)C3)n1] | 6-(4,6-dimethylpyrimidin-2-yl)-3-{[2-(1-methylethoxy)-phenyl]carbonyl}-3,6-diazabicyclo[3.2.1]octane | 381.2 |
| 17 | 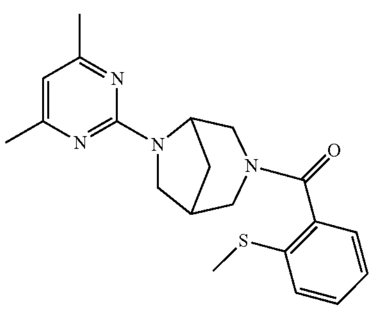 [SMILES: CSc1ccccc1C(=O)N1CC2CC(C1)N(c1nc(C)cc(C)n1)C2] | 6-(4,6-dimethylpyrimidin-2-yl)-3-{[2-(methylsulfanyl)-phenyl]carbonyl}-3,6-diazabicyclo[3.2.1]octane | 369.2 |
| 18 | 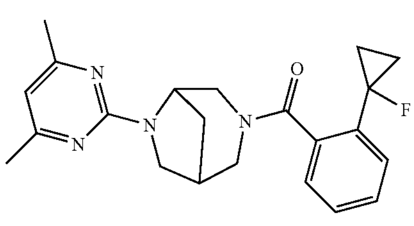 [SMILES: Cc1cc(C)nc(N2CC3CC2CN(C(=O)c2ccccc2C2(F)CC2)C3)n1] | 6-(4,6-dimethylpyrimidin-2-yl)-3-{[2-(1-fluorocyclopropyl)-phenyl]carbonyl}-3,6-diazabicyclo[3.2.1]octane | 381.2 |

TABLE 2-continued

The following compounds were prepared using the foregoing methodology and general procedure described in Example 10, but substituting the appropriate benzoic acid in Step 3, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 19 | 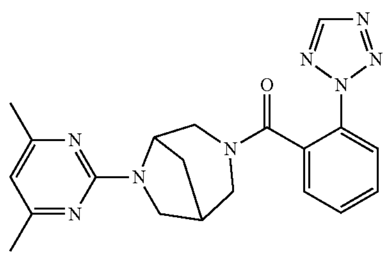 [SMILES: Cc1cc(C)nc(N2CC3CC2CN(C(=O)c2ccccc2-n2ncnn2)C3)n1] | 6-(4,6-dimethylpyrimidin-2-yl)-3-{[2-(2H-tetrazol-2-yl)phenyl]carbonyl}-3,6-diazabicyclo[3.2.1]octane | 391.2 |
| 20 | 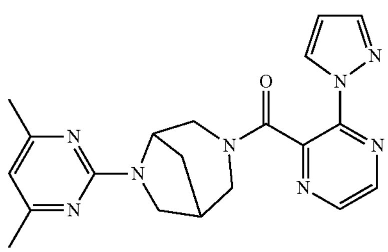 [SMILES: Cc1cc(C)nc(N2CC3CC2CN(C(=O)c2nccnc2-n2cccn2)C3)n1] | 6-(4,6-dimethylpyrimidin-2-yl)-3-{[3-(1H-pyrazol-1-yl)pyrazin-2-yl]carbonyl}-3,6-diazabicyclo[3.2.1]octane | 391.4 |
| 21 | 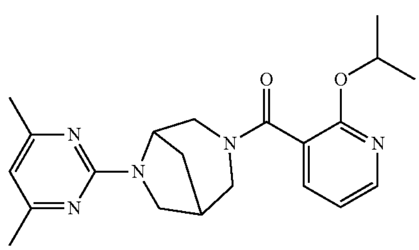 [SMILES: Cc1cc(C)nc(N2CC3CC2CN(C(=O)c2cccnc2OC(C)C)C3)n1] | 6-(4,6-dimethylpyrimidin-2-yl)-3-{[2-(1-methylethoxy)pyridin-3-yl]carbonyl}-3,6-diazabicyclo[3.2.1]octane | 382.4 |
| 22 | 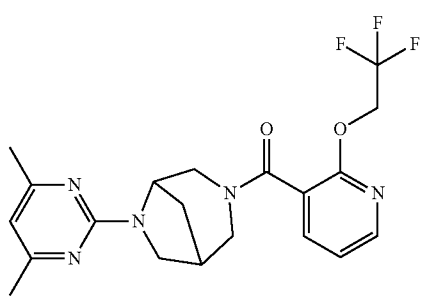 [SMILES: Cc1cc(C)nc(N2CC3CC2CN(C(=O)c2cccnc2OCC(F)(F)F)C3)n1] | 6-(4,6-dimethylpyrimidin-2-yl)-3-{[2-(2,2,2-trifluoroethoxy)pyridin-3-yl]carbonyl}-3,6-diazabicyclo[3.2.1]octane | 422.4 |
| 23 | 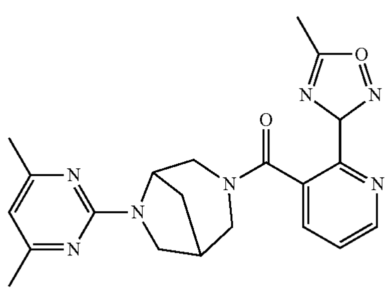 | 6-(4,6-dimethylpyrimidin-2-yl)-3-{[2-(5-methyl-1,2,4-oxadiazol-3-yl)pyridin-3-yl]carbonyl}-3,6-diazabicyclo[3.2.1]octane | 406.4 |

TABLE 2-continued

The following compounds were prepared using the foregoing methodology and general procedure described in Example 10, but substituting the appropriate benzoic acid in Step 3, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 24 | 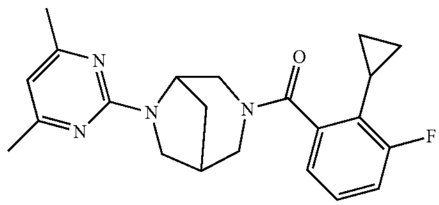 [SMILES: Cc1cc(C)nc(N2CC3CC2CN(C(=O)c2cccc(F)c2C2CC2)C3)n1] | (2-cyclopropyl-3-fluorophenyl)(6-(4,6-dimethylpyrimidin-2-yl)-3,6-diazabicyclo[3.2.1]octan-3-yl)methanone | 381.2 |
| 25 | 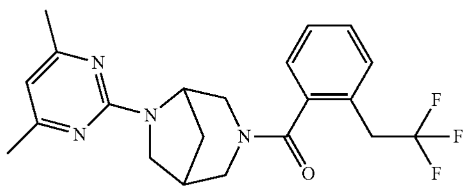 [SMILES: Cc1cc(C)nc(N2CC3CC2CN(C(=O)c2ccccc2CC(F)(F)F)C3)n1] | 6-(4,6-dimethylpyrimidin-2-yl)-3-{[2-(2,2,2-trifluoroethyl)phenyl]carbonyl}-3,6-diazabicyclo[3.2.1]octane | 405.4 |
| 26 | 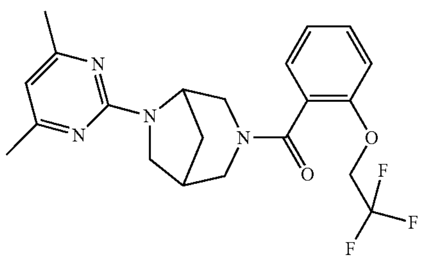 [SMILES: Cc1cc(C)nc(N2CC3CC2CN(C(=O)c2ccccc2OCC(F)(F)F)C3)n1] | 6-(4,6-dimethylpyrimidin-2-yl)-3-{[2-(2,2,2-trifluoroethoxy)-phenyl]carbonyl}-3,6-diazabicyclo[3.2.1]octane | 421.4 |
| 27 | 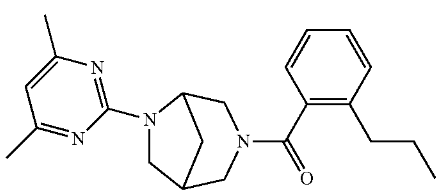 [SMILES: CCCc1ccccc1C(=O)N1CC2CC(C1)N(c1nc(C)cc(C)n1)C2] | 6-(4,6-dimethylpyrimidin-2-yl)-3-[(2-propylphenyl)carbonyl]-3,6-diazabicyclo[3.2.1]octane | 365.4 |
| 28 | 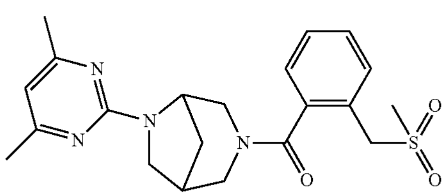 [SMILES: Cc1cc(C)nc(N2CC3CC2CN(C(=O)c2ccccc2CS(C)(=O)=O)C3)n1] | 6-(4,6-dimethylpyrimidin-2-yl)-3-({2-[(methylsulfonyl)methyl]phenyl}carbonyl)-3,6-diazabicyclo[3.2.1]octane | 415.4 |
| 29 | 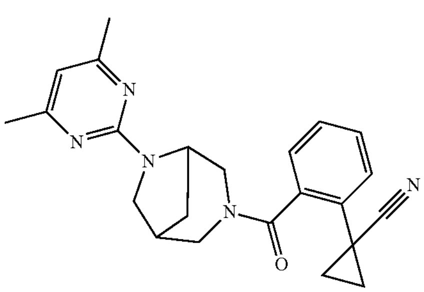 [SMILES: Cc1cc(C)nc(N2CC3CC2CN(C(=O)c2ccccc2C2(C#N)CC2)C3)n1] | 1-(2-{[6-(4,6-dimethylpyrimidin-2-yl)-3,6-diazabicyclo[3.2.1]oct-3-yl]carbonyl}-phenyl)-cyclopropanecarbonitrile | 388.4 |

TABLE 2-continued

The following compounds were prepared using the foregoing methodology and general procedure described in Example 10, but substituting the appropriate benzoic acid in Step 3, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 30 | 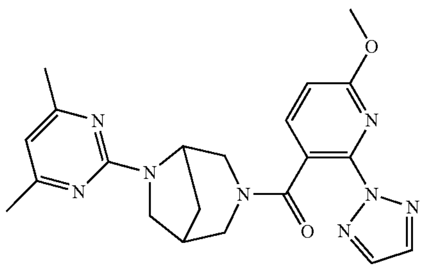 [SMILES: COc1ccc(C(=O)N2CC3CC(C2)N(c2nc(C)cc(C)n2)C3)c(-n2nccn2)n1] | 6-(4,6-dimethylpyrimidin-2-yl)-3-{[6-methoxy-2-(2H-1,2,3-triazol-2-yl)pyridin-3-yl]carbonyl}-3,6-diazabicyclo[3.2.1]octane | 421.4 |
| 31 | 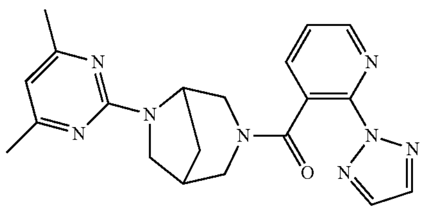 [SMILES: Cc1cc(C)nc(N2CC3CC2CN(C(=O)c2cccnc2-n2nccn2)C3)n1] | 6-(4,6-dimethylpyrimidin-2-yl)-3-{[2-(2H-1,2,3-triazol-2-yl)pyridin-3-yl]carbonyl}-3,6-diazabicyclo[3.2.1]octane | 391.4 |
| 32 | 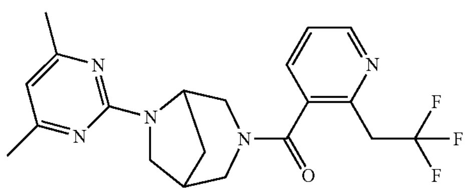 [SMILES: Cc1cc(C)nc(N2CC3CC2CN(C(=O)c2cccnc2CC(F)(F)F)C3)n1] | 6-(4,6-dimethylpyrimidin-2-yl)-3-{[2-(2,2,2-trifluoroethyl)pyridin-3-yl]carbonyl}-3,6-diazabicyclo[3.2.1]octane | 406.4 |
| 33 | 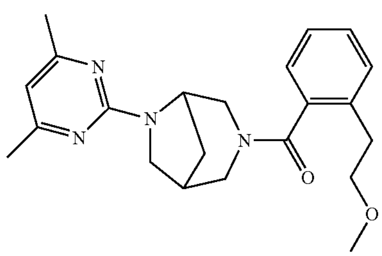 [SMILES: COCCc1ccccc1C(=O)N1CC2CC(C1)N(c1nc(C)cc(C)n1)C2] | 6-(4,6-dimethylpyrimidin-2-yl)-3-{[2-(2-methoxyethyl)phenyl]carbonyl}-3,6-diazabicyclo[3.2.1]octane | 381.4 |
| 34 | 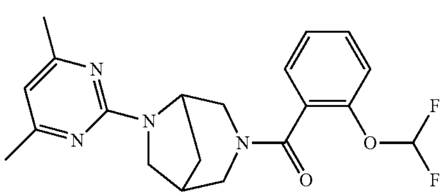 [SMILES: Cc1cc(C)nc(N2CC3CC2CN(C(=O)c2ccccc2OC(F)F)C3)n1] | 3-{[2-(difluoromethoxy)phenyl]carbonyl}-6-(4,6-dimethylpyrimidin-2-yl)-3,6-diazabicyclo[3.2.1]octane | 389.4 |
| 35 | 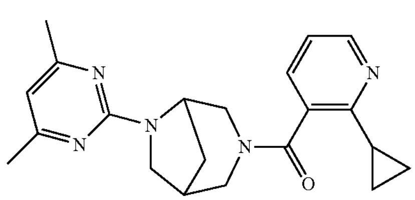 [SMILES: Cc1cc(C)nc(N2CC3CC2CN(C(=O)c2cccnc2C2CC2)C3)n1] | 3-[(2-cyclopropylpyridin-3-yl)carbonyl]-6-(4,6-dimethylpyrimidin-2-yl)-3,6-diazabicyclo[3.2.1]octane | 364.4 |

TABLE 2-continued

The following compounds were prepared using the foregoing methodology and general procedure described in Example 10, but substituting the appropriate benzoic acid in Step 3, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 36 | 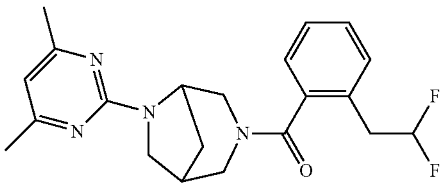 | 3-{[2-(2,2-difluoroethyl)phenyl]carbonyl}-6-(4,6-dimethylpyrimidin-2-yl)-3,6-diazabicyclo[3.2.1]octane | 387.4 |
| 37 | 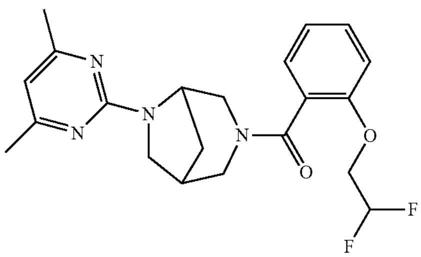 [SMILES: Cc1cc(C)nc(N2CC3CC2CN(C(=O)c2ccccc2OCC(F)F)C3)n1] | 3-{[2-(2,2-difluoroethoxy)-phenyl]carbonyl}-6-(4,6-dimethylpyrimidin-2-yl)-3,6-diazabicyclo[3.2.1]octane | 403.4 |

Example 38

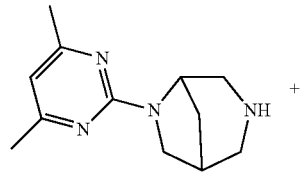

10-2

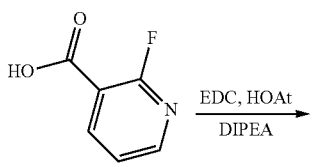

EDC, HOAt
DIPEA

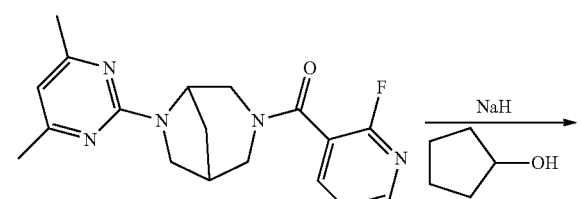

38-1

NaH

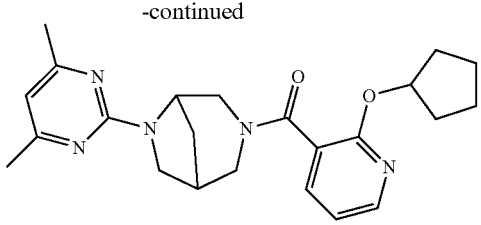

Example 38

3-[2-(Cyclopentyloxy)pyridin-3-yl)]-6-(4,6-dimethylpyrimidin-2-yl)-3,6-diazabicyclo-[3.2.1]octan-3-yl)methanone Step 1: (6-(4,6-dimethylpyrimidin-2-yl)-3,6-diazabicyclo[3.2.1]octan-3-yl)(2-fluoropyridin-3-yl)methanone (38-1)

A solution of 6-(4,6-dimethylpyrimidin-2-yl)-3,6-diazabicyclo[3.2.1]octane 10-2 (75 mg, 0.34 mmol), 2-fluoronicotinic acid (72.7 mg, 0.51 mmol), EDC (99 mg, 0.51 mmol), HOAt (70.1 mg, 0.51 mmol), and N,N-diisopropylethylamine (0.180 mL, 1.03 mmol) in DMF (1 mL) was stirred at 50° C. for 24 h. The cooled mixture was diluted with EtOAc (50 mL) washed with saturated NaHCO₃ solution (3×10 mL) and brine solution (10 mL). The organic layer was dried over MgSO₄ and concentrated in vacuo to give an orange oil that was purified by silica gel chromatography (0-100% EtOAc/hexanes, 20 minutes) to afford 38-1 as a solid. MS (ESI) m/z: 342.4 (M+H).

Step 2: 3-[2-(Cyclopentyloxy)pyridin-3-yl)]-6-(4,6-dimethylpyrimidin-2-yl)-3,6-diazabicyclo-[3.2.1]octan-3-yl)methanone)

To a solution of cyclopentanol (12.1 mg, 0.14 mmol) in DMF (0.25 mL) was added NaH (4.2 mg, 0.11 mmol, 60% oil dispersion). The resulting heterogeneous mixture was stirred at room temperature for 15 min and 38-1 (12 mg, 0.035 mmol) was added. After stirring for 2 h at 80° C., the cooled reaction mixture was purified on reversed phase HPLC (sunfire prep C18 OBP 10 μm, 30×150 mm column, 10-70% CH3CN/water with 0.1% TFA, 15 min). The combined product fractions were neutralized with saturated NaHCO$_3$ solution, extracted with EtOAc (3×10 mL) and the organic layer was dried over MgSO$_4$ and concentrated in vacuo to give Example 38 as a solid. MS (ESI) m/z: 408.4 (M+H).

TABLE 3

The following compounds were prepared using the foregoing methodology and general procedure described in Example 38, but substituting the appropriate alcohol in Step 2, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 39 | 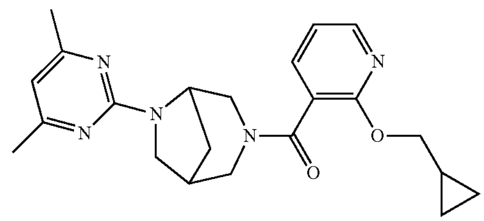 [SMILES: Cc1cc(C)nc(N2CC3CC2CN(C(=O)c2cccnc2OCC2CC2)C3)n1] | 3-{[2-(cyclopropyl-methoxy)pyridin-3-yl]carbonyl}-6-(4,6-dimethylpyrimidin-2-yl)-3,6-diazabicyclo-[3.2.1]octane | 394.4 |
| 40 | 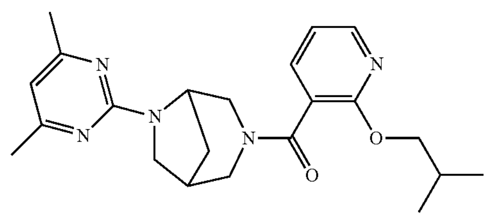 [SMILES: Cc1cc(C)nc(N2CC3CC2CN(C(=O)c2cccnc2OCC(C)C)C3)n1] | 6-(4,6-dimethyl-pyrimidin-2-yl)-3-{[2-(2-methylpropoxy)pyridin-3-yl]carbonyl}-3,6-diazabicyclo[3.2.1]octane | 396.4 |
| 41 | 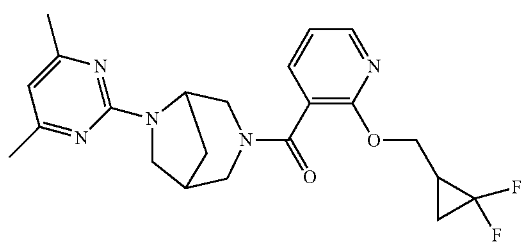 [SMILES: Cc1cc(C)nc(N2CC3CC2CN(C(=O)c2cccnc2OCC2CC2(F)F)C3)n1] | 3-({2-[(2,2-difluorocyclopropyl)methoxy]pyridin-3-yl}carbonyl)-6-(4,6-dimethylpyrimidin-2-yl)-3,6-diazabicyclo[3.2.1]octane | 430.4 |
| 42 | 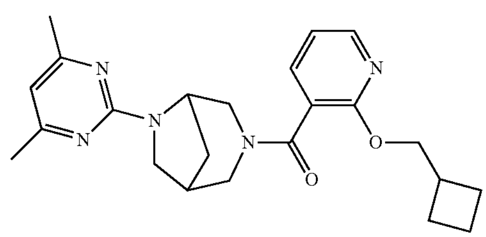 [SMILES: Cc1cc(C)nc(N2CC3CC2CN(C(=O)c2cccnc2OCC2CCC2)C3)n1] | 3-{[2-(cyclobutylmethoxy)pyridin-3-yl]carbonyl}-6-(4,6-dimethylpyrimidin-2-yl)-3,6-diazabicyclo[3.2.1]octane | 408.4 |
| 43 | 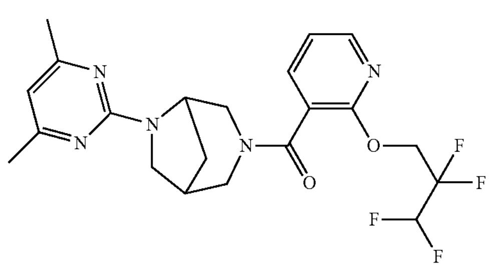 [SMILES: Cc1cc(C)nc(N2CC3CC2CN(C(=O)c2cccnc2OCC(F)(F)C(F)F)C3)n1] | 6-(4,6-dimethylpyrimidin-2-yl)-3-{[2-(2,2,3,3-tetrafluoropropoxy)pyridin-3-yl]carbonyl}-3,6-diazabicyclo[3.2.1]octane | 454.3 |

TABLE 3-continued

The following compounds were prepared using the foregoing methodology and general procedure described in Example 38, but substituting the appropriate alcohol in Step 2, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 44 | 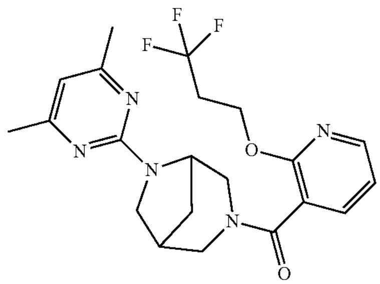 [SMILES: Cc1cc(C)nc(N2CC3CC2CN(C(=O)c2cccnc2OCCC(F)(F)F)C3)n1] | 6-(4,6-dimethylpyrimidin-2-yl)-3-{[2-(3,3,3-trifluoropropoxy)pyridin-3-yl]carbonyl}-3,6-diazabicyclo[3.2.1]octane | 436.4 |
| 45 | 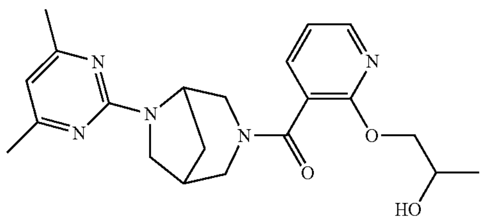 [SMILES: Cc1cc(C)nc(N2CC3CC2CN(C(=O)c2cccnc2OCC(C)O)C3)n1] | 1-[(3-{[6-(4,6-dimethylpyrimidin-2-yl)-3,6-diazabicyclo[3.2.1]oct-3-yl]carbonyl}pyridin-2-yl)oxy]propan-2-ol | 398.4 |

Example 46

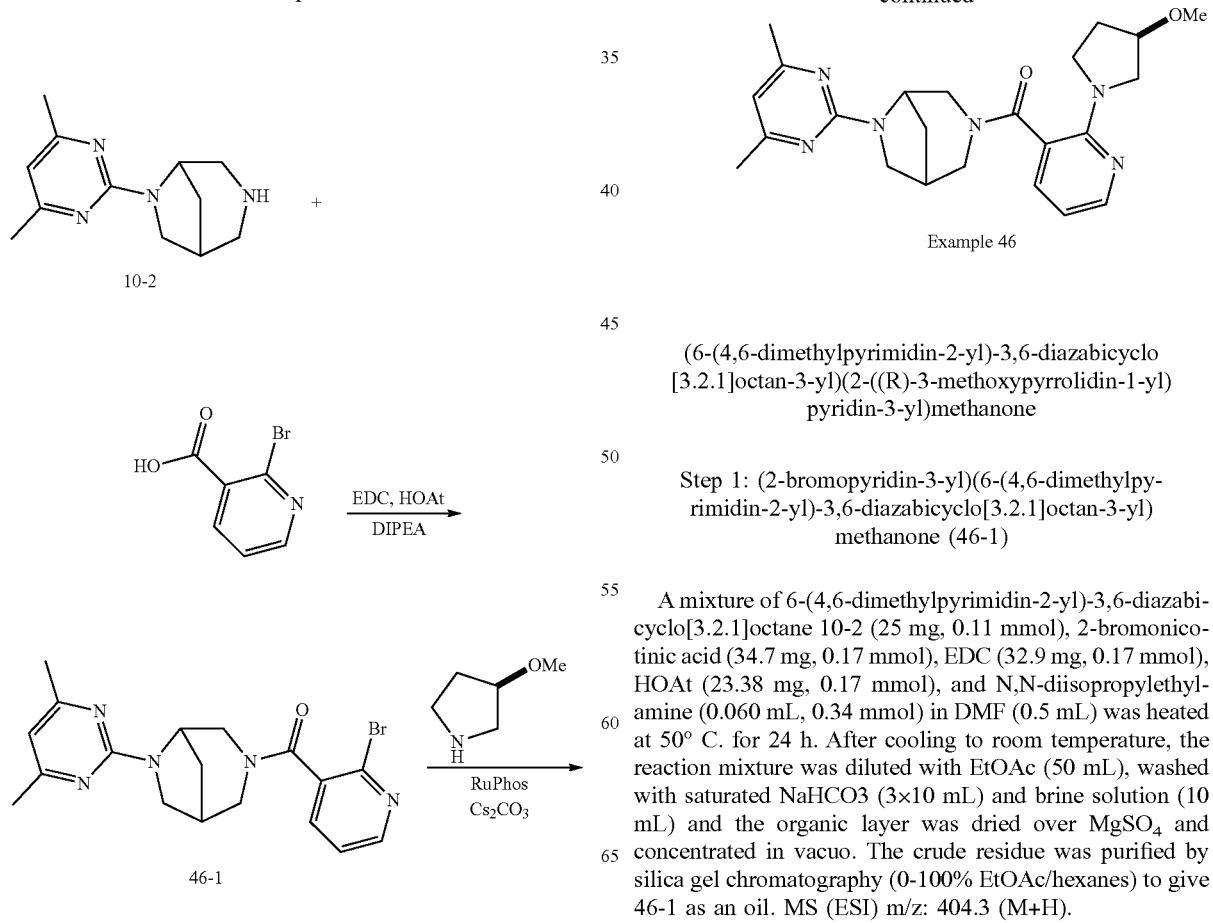

Example 46

(6-(4,6-dimethylpyrimidin-2-yl)-3,6-diazabicyclo[3.2.1]octan-3-yl)(2-((R)-3-methoxypyrrolidin-1-yl)pyridin-3-yl)methanone Step 1: (2-bromopyridin-3-yl)(6-(4,6-dimethylpyrimidin-2-yl)-3,6-diazabicyclo[3.2.1]octan-3-yl)methanone (46-1)

A mixture of 6-(4,6-dimethylpyrimidin-2-yl)-3,6-diazabicyclo[3.2.1]octane 10-2 (25 mg, 0.11 mmol), 2-bromonicotinic acid (34.7 mg, 0.17 mmol), EDC (32.9 mg, 0.17 mmol), HOAt (23.38 mg, 0.17 mmol), and N,N-diisopropylethylamine (0.060 mL, 0.34 mmol) in DMF (0.5 mL) was heated at 50° C. for 24 h. After cooling to room temperature, the reaction mixture was diluted with EtOAc (50 mL), washed with saturated NaHCO3 (3×10 mL) and brine solution (10 mL) and the organic layer was dried over MgSO$_4$ and concentrated in vacuo. The crude residue was purified by silica gel chromatography (0-100% EtOAc/hexanes) to give 46-1 as an oil. MS (ESI) m/z: 404.3 (M+H).

Step 2: (6-(4,6-dimethylpyrimidin-2-yl)-3,6-diazabicyclo[3.2.1]octan-3-yl)(2-((R)-3-methoxypyrrolidin-1-yl)pyridin-3-yl)methanone (Example 46)

To a solution of (2-bromopyridin-3-yl)(6-(4,6-dimethylpyrimidin-2-yl)-3,6-diazabicyclo[3.2.1]octan-3-yl)methanone 46-1 (15 mg, 0.037 mmol) in dioxane (0.25 mL) was added (S)-3-methoxypyrrolidine (7.5 mg, 0.075 mmol), chloro(2-dicyclohexylphosphino-2',6'-di-i-propoxy-1,1'-biphenyl)[(2-(2-aminoethylphenyl)]palladium (II) methyl-t-butyl ether adduct (6.09 mg, 7.46 μmol), and cesium carbonate (36.4 mg, 0.112 mmol) and the reaction was heated in a sealed tube at 100° C. for 30 min. The reaction was cooled to room temperature and solids were filtered through a pad of Celite, rinsing with MeOH. The filtrate was concentrated in vacuo and the crude residue was purified on reversed phase HPLC (sunfire prep C18 OBP 10 μm, 30×150 mm column, 5-100% CH₃CN/water with 0.1% TFA, 20 min). The combined product fractions were neutralized with saturated NaHCO₃ solution, extracted with EtOAc (3×10 mL) and the organic layer was dried over MgSO₄ and concentrated in vacuo to give the title compound as an oil. MS (ESI) m/z: 423.4 (M+H).

Example 47

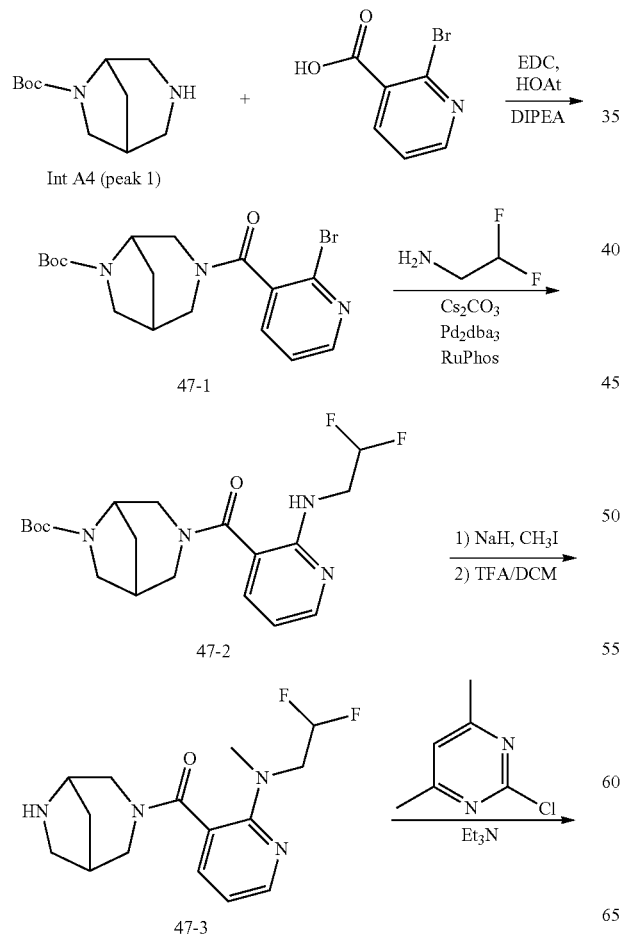

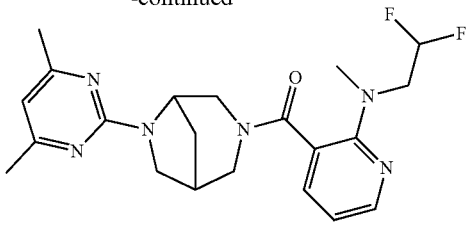

Example 47

2-((2,2-difluoroethyl)(methylamino)pyridin-3-yl)(6-(4,6-dimethylpyridin-2-yl)-3,6-diazabicyclo[3.2.1]octan-3-yl)methanone Step 1: tert-butyl 3-(2-bromonicotinoyl)-3,6-diazabicyclo[3.2.1]octane-6-carboxylate (47-1)

A mixture of tent-butyl 3,6-diazabicyclo[3.2.1]octane-6-carboxylate Intermediate A4 (peak 1) (150 mg, 0.71 mmol), 2-bromonicotinic acid (214 mg, 1.06 mmol), EDC (203 mg, 1.06 mmol), HOAt (144 mg, 1.06 mmol), and N,N-diisopropylethylamine (0.37 mL, 2.12 mmol) in acetonitrile (1.5 mL) was stirred at room temperature for 24 h. The crude reaction mixture was concentrated in vacuo and purified by silica gel chromatography (0-100% EtOAc/hexanes, 20 minutes) to provide 47-1 as an oil. MS (ESI) m/z: 396.3 (M+H).

Step 2: tert-butyl 3-(2-((2,2-difluoroethyl)amino)nicotinoyl)-3,6-diazabicyclo[3.2.1]octane-6-carboxylate (47-2)

To a solution of tent-butyl 3-(2-bromonicotinoyl)-3,6-diazabicyclo[3.2.1]octane-6-carboxylate 47-1 (50 mg, 0.13 mmol) in dioxane (0.25 mL) was added 2,2-difluoroethanamine (15.3 mg, 0.19 mmol), 2-dicyclohexylphosphino-2',6'-di-i-propoxy-1,1'-biphenyl (5.9 mg, 0.013 mmol), tris(dibenzylidineacetone)dipalladium(0) (2.9 mg, 3.15 μmol) and cesium carbonate (82 mg, 0.25 mmol) while degassing under a stream of nitrogen. The mixture was stirred at 100° C. in a sealed tube for 24 h. The reaction mixture was cooled and filtered through a pad of Celite and the pad was washed with 5 ml MeOH. The filtrate was concentrated in vacuo and the crude mixture was purified by silica gel chromatography (0-100% EtOAc/hexanes, 20 minutes) to give 47-2 as an oil. MS (ESI) m/z: 397.4 (M+H).

Step 3: 3,6-diazabicyclo[3.2.1]octan-3-yl(2-(2,2-difluoroethyl)(methyl)amino)pyridin-3-yl)methanone (47-3)

To a mixture of tent-butyl 3-(2-((2,2-difluoroethyl)amino)nicotinoyl)-3,6-diazabicyclo[3.2.1]octane-6-carboxylate 47-2 (30 mg, 0.076 mmol) in DMF (1 mL) was added NaH (4.5 mg, 0.114 mmol) and the resulting heterogeneous mixture was stirred for 10 min at room temperature. Iodomethane (5.7 μL, 0.09 mmol) was added and the pale yellow solution was stirred for 10 min. The crude reaction mixture was purified by reversed phase HPLC (sunfire prep C18 OBP 10 μm, 30×150 mm column, 10-70% CH₃CN/water with 0.1% TFA, 20 min). Additional TFA (1 mL) was added to HPLC fractions which were left to age for 30 min at room tempature. Concentration in vacuo provided 47-3 as an oil (TFA salt). MS (ESI) m/z: 311.3 (M+H).

Step 4: ((2,2-difluoroethyl)(methylamino)pyridin-3-yl)(6-(4,6-dimethylpyridin-2-yl)-3,6-diazabicyclo[3.2.1]octan-3-yl)methanone (Example 47)

A mixture of 3,6-diazabicyclo[3.2.1]octan-3-yl(2-((2,2-difluoroethyl)(methyl)amino)pyridin-3-yl)methanone 47-3 (28 mg, 0.069 mmol), 2-chloro-4,6-dimethylpyrimidine (14.7 mg, 0.103 mmol), and triethylamine (0.048 mL, 0.344 mmol) in acetonitrile (5 mL) was heated in a sealed tube at 85° C. for 24 h. The cooled mixture was purified by reversed phase HPLC (sunfire prep C18 OBP 10 μm, 30×150 mm column, 10-70% CH$_3$CN/water with 0.1% TFA, 20 min). The combined product fractions were neutralized with saturated NaHCO$_3$ solution, extracted with EtOAc (3×10 mL) and the organic layer was dried over MgSO$_4$ and concentrated in vacuo to give the title compound as an oil. MS (ESI) m/z: 417.4 (M+H).

Example 48

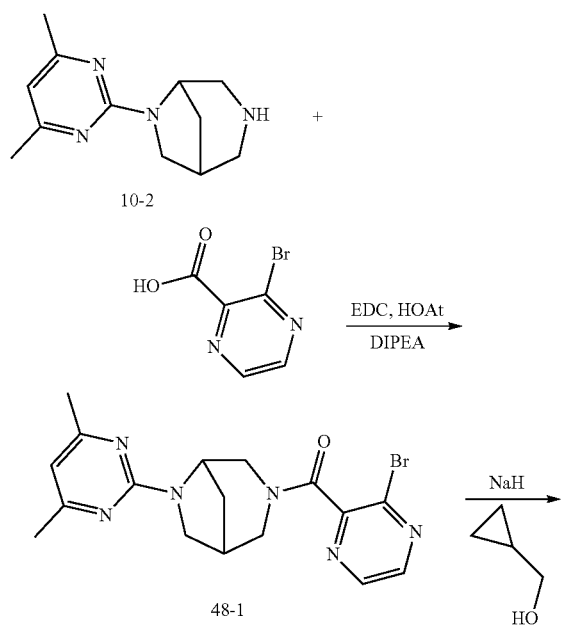

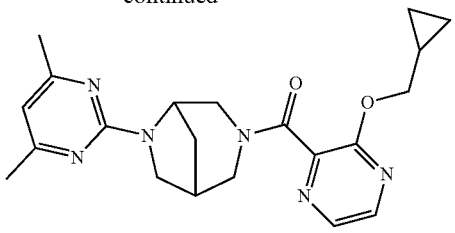

Example 48

(3-(cyclopropylmethoxy)pyrazin-2-yl)(6-(4,6-dimethylpyrimidin-2-yl)-3,6-diazabicyclo[3.2.1]octan-3-yl)methanone

Step 1: (3-bromopyrazin-2-yl)(6-(4,6-dimethylpyrimidin-2-yl)-3,6-diazabicyclo[3.2.1]octan-3-yl)methanone (48-1)

A mixture of 6-(4,6-dimethylpyrimidin-2-yl)-3,6-diazabicyclo[3.2.1]octane 10-2 (150 mg, 0.69 mmol), 3-bromopyrazine-2-carboxylic acid (167 mg, 0.83 mmol), EDC (198 mg, 1.03 mmol), HOAt (140 mg, 1.03 mmol), and N,N-diisopropylethylamine (0.36 mL, 2.06 mmol) in acetonitrile (1 mL) was stirred at room temperature for 24 h. The reaction was concentrated in vacuo and the crude residue was purified by silica gel chromatography (0-100% EtOAc/hexanes, 20 min) to give 48-1 as an oil. MS (ESI) m/z: 403.3 (M+H).

Step 2: (3-(cyclopropylmethoxy)pyrazin-2-yl)-(6-(4,6-dimethylpyrimidin-2-yl)-3,6-diazabicyclo[3.2.1]octan-3-yl)methanone (Example 48)

To a solution of cyclopropylmethanol (8.9 mg, 0.124 mmol) in DMF (0.25 mL) was added NaH (4.0 mg, 0.10 mmol) and the mixture was stirred for 10 min. (3-bromopyrazin-2-yl)(6-(4,6-dimethylpyrimidin-2-yl)-3,6-diazabicyclo[3.2.1]octan-3-yl)methanone 48-1 (10 mg, 0.025 mmol) was added in one portion and the reaction was stirred at room temperature for 30 min. The crude reaction mixture was purified on reversed phase HPLC (sunfire prep C18 OBP 10 μm, 30×150 mm column, 10-70% CH$_3$CN/water with 0.1% TFA, 20 min). The combined product fractions were neutralized with saturated NaHCO$_3$ solution, extracted with EtOAc (3×10 mL) and the organic layer was dried over MgSO$_4$ and concentrated in vacuo to give the title compound as a solid. MS (ESI) m/z: 395.4 (M+H).

TABLE 4

The following compounds were prepared using the foregoing methodology and general procedure described in Example 48, but substituting the appropriate alcohol in Step 2, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 49 | 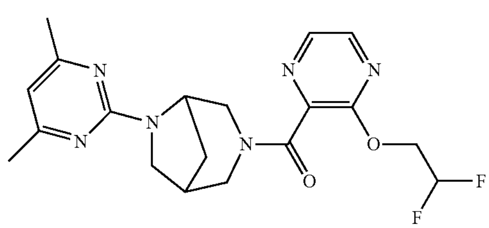 [SMILES: Cc1cc(C)nc(N2CC3CC2CN(C(=O)c2nccnc2OCC(F)F)C3)n1] | 3-{[3-[2,2-difluoroethoxy)pyrazin-2-yl]carbonyl}-6-(4,6-dimethylpyrimidin-2-yl)-3,6-diazabicyclo[3.2.1]octane | 405.4 |

TABLE 4-continued

The following compounds were prepared using the foregoing methodology and general procedure described in Example 48, but substituting the appropriate alcohol in Step 2, as described in the Reaction Schemes and Examples herein. The requisite starting materials were commercially available, described in the literature or readily synthesized by one skilled in the art of organic synthesis from commercially available reagents using conventional reactions without undue experimentation.

| Example | Structure | Name | LRMS [M + H] |
|---|---|---|---|
| 50 | 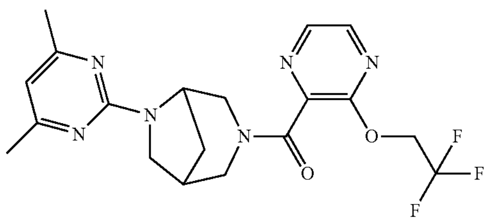 [SMILES: Cc1cc(C)nc(N2CC3CC2CN(C(=O)c2nccnc2OCC(F)(F)F)C3)n1] | 6-(4,6-dimethylpyrimidin-2-yl)-3-{[3-(2,2,2-trifluoroethoxy)pyrazin-2-yl]carbonyl}-3,6-diazabicyclo[3.2.1]octane | 423.4 |
| 51 | 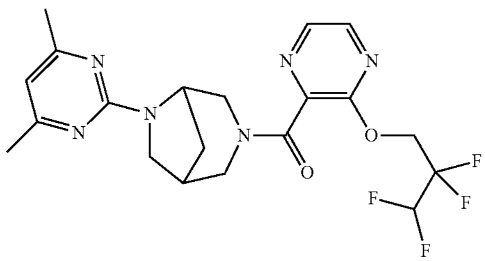 [SMILES: Cc1cc(C)nc(N2CC3CC2CN(C(=O)c2nccnc2OCC(F)(F)C(F)F)C3)n1] | (6-(4,6-dimethylpyrimidin-2-yl)-3,6-diazabicyclo[3.2.1]octan-3-yl)(3-(2,2,3,3-tetrafluoropropoxy)pyrazin-2-yl)methanone | 455.4 |
| 52 | 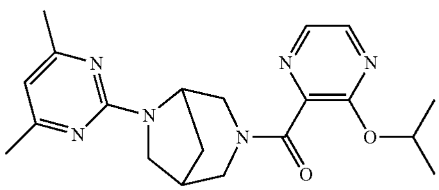 [SMILES: Cc1cc(C)nc(N2CC3CC2CN(C(=O)c2nccnc2OC(C)C)C3)n1] | 6-(4,6-dimethylpyrimidin-2-yl)-3-{[3-(1-methylethoxy)pyrazin-2-yl]carbonyl}-3,6-diazabicyclo[3.2.1]octane | 383.4 |
| 53 | 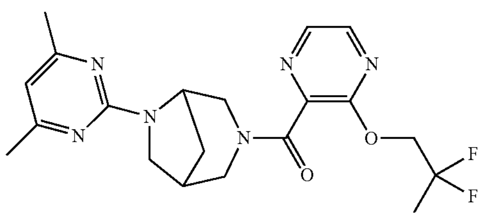 [SMILES: Cc1cc(C)nc(N2CC3CC2CN(C(=O)c2nccnc2OCC(C)(F)F)C3)n1] | (3-(2,2-difluoropropoxy)pyrazin-2-yl)(6-(4,6-dimethylpyrimidin-2-yl)-3,6-diazabicyclo[3.2.1]octan-3-yl)methanone | 419.4 |

TABLE 4

The following table shows representative data for the compounds of the Examples as orexin receptor antagonists as determined by the assays described herein.

| Example | $OX_2R$ FLIPR (nM) | $OX_1R$ FLIPR (nM) | Fold Selective |
|---|---|---|---|
| 1 | 23 | 1865 | 81 |
| 2 | 46 | >10000 | 217 |
| 3 | 18 | 3207 | 178 |
| 4 | 19 | 3304 | 174 |
| 5 | 81 | >10000 | 123 |
| 6 | 74 | >10000 | 135 |
| 7 | 61 | >10000 | 164 |
| 8 | 29 | 5860 | 202 |
| 9 | 15 | 1830 | 122 |
| 10 | 46 | 3409 | 74 |
| 11 | 13 | 613 | 47 |
| 12 | 22 | 1035 | 47 |
| 13 | 41 | 3554 | 87 |
| 14 | 26 | 1453 | 56 |
| 15 | 30 | 1529 | 51 |
| 16 | 16 | 982 | 61 |
| 17 | 27 | 2472 | 92 |
| 18 | 15 | 872 | 58 |
| 19 | 36 | 1598 | 44 |
| 20 | 50 | 3400 | 68 |
| 21 | 18 | 2667 | 148 |
| 22 | 13 | 1042 | 80 |
| 23 | 103 | >10000 | 97 |
| 24 | 17 | 743 | 44 |
| 25 | 17 | 2021 | 119 |
| 26 | 10 | 1136 | 114 |

TABLE 4-continued

The following table shows representative data for the compounds of the Examples as orexin receptor antagonists as determined by the assays described herein.

| Example | OX$_2$R FLIPR (nM) | OX$_1$R FLIPR (nM) | Fold Selective |
|---|---|---|---|
| 27 | 14 | 1177 | 84 |
| 28 | 47 | >10000 | 213 |
| 29 | 13 | 1120 | 86 |
| 30 | 117 | >10000 | 85 |
| 31 | 90 | >10000 | 111 |
| 32 | 58 | >10000 | 172 |
| 33 | 44 | 3988 | 91 |
| 34 | 24 | 2678 | 112 |
| 35 | 47 | >10000 | 213 |
| 36 | 15 | 2087 | 139 |
| 37 | 14 | 851 | 61 |
| 38 | 23 | 1078 | 47 |
| 39 | 13 | 1374 | 106 |
| 40 | 16 | 648 | 41 |
| 41 | 12 | 584 | 49 |
| 42 | 15 | 628 | 42 |
| 43 | 5 | 206 | 41 |
| 44 | 21 | 932 | 44 |
| 45 | 90 | >10000 | 111 |
| 46 | 90 | >10000 | 111 |
| 47 | 29 | 7560 | 261 |
| 48 | 37 | 3829 | 103 |
| 49 | 33 | 3864 | 117 |
| 50 | 36 | >10000 | 278 |
| 51 | 24 | 2687 | 112 |
| 52 | 60 | >10000 | 167 |
| 53 | 39 | 6448 | 165 |

With respect to other diazepane compounds such as those disclosed in U.S. Pat. Nos. 8,618,102 and 8,685,961, it would be desirable that the present compounds exhibit unexpected properties, such as increased selectivity at the orexin-2 receptor relative to the orexin-1 receptor. For example, relative to diazepane compounds of U.S. Pat. Nos. 8,618,102 and 8,685,961, the compounds of the examples possess greater selectivity for the orexin-2 receptor than for the orexin-1 receptor.

For example, the following diazepane compound "B-3" is disclosed in U.S. Pat. No. 8,685,961, and possesses greater selectivity for the orexin-1 receptor than for the orexin-2 receptor:

Example B-3

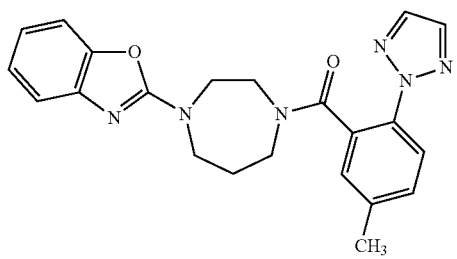

hOX2R IC$_{50}$ = 115 nM
hOX1R IC$_{50}$ = 18.5 nM
Fold Selectivity for
hOX2R vs. hOX1R = 0.16

As indicated by the data herein, the compounds of the present examples provide greater functional selectivity for the orexin-2 receptor over the orexin-1 receptor. The distinction in potency between the orexin-2 receptor and the orexin-1 receptor in the whole cell FLIPR functional assay provides enhanced predictive value for determining in vivo efficacy. Increasing the functional selectivity for the orexin-2 receptor reduces the potential for dual receptor antagonism in vivo. Such greater functional selectivity may provide benefits over other orexin receptor antagonists that are known in the art.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula Ia:

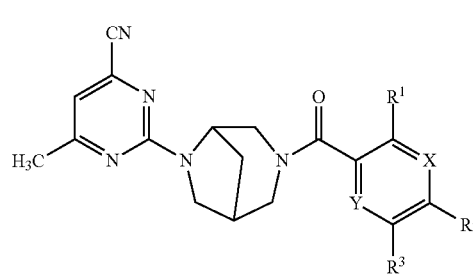

Ia or a compound of the formula Ib:

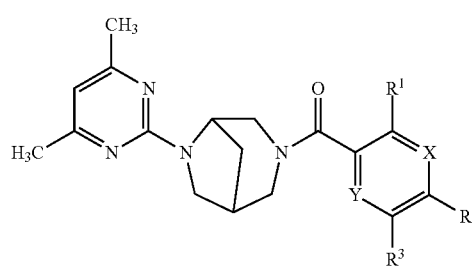

Ib wherein:
X is CH or N;
Y is CH or N;
R$^1$ is selected from the group consisting of:
(1) hydrogen,
(2) halogen,
(3) hydroxyl,
(4) —(C═O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from R$^4$,
(5) —(C═O)$_m$—O$_n$—C$_{3-6}$cycloalkyl, where the cycloalkyl is unsubstituted or substituted with one or more substituents selected from R$^4$,
(6) —(C═O)$_m$—C$_{2-4}$alkenyl, where the alkenyl is unsubstituted or substituted with one or more substituents selected from R$^4$,
(7) —(C═O)$_m$—C$_{2-4}$alkynyl, where the alkynyl is unsubstituted or substituted with one or more substituents selected from R$^4$,
(8) —(C═O)$_m$—O$_n$-phenyl or —(C═O)$_m$—O$_n$-naphthyl, where the phenyl or naphthyl is unsubstituted or substituted with one or more substituents selected from R$^4$, (9) —(C═O)$_m$—O$_n$-heterocycle, where the heterocycle is unsubstituted or substituted with one or more substituents selected from R$^4$,
(10) —(C═O)$_m$—NR$^{10}$R$^{11}$, wherein R$^{10}$ and R$^{11}$ are independently selected from the group consisting of:
(a) hydrogen,
(b) C$_{1-6}$alkyl, which is unsubstituted or substituted with R$^4$,
(c) C$_{3-6}$alkenyl, which is unsubstituted or substituted with R$^4$,
(d) C$_{3-6}$alkynyl, which is unsubstituted or substituted with R$^4$,
(e) C$_{3-6}$cycloalkyl which is unsubstituted or substituted with R$^4$,
(f) phenyl, which is unsubstituted or substituted with R$^4$, and
(g) heterocycle, which is unsubstituted or substituted with R$^4$,
(11) —S(O)$_2$—NR$^{10}$R$^{11}$,
(12) —S(O)$_q$—R$^{12}$, where q is 0, 1 or 2 and where R$^{12}$ is selected from the definitions of R$^{10}$ and R$^{11}$,
(13) —CO$_2$H,
(14) —CN, and
(15) —NO$_2$;
R$^2$ is selected from the group consisting of:
(1) hydrogen,
(2) hydroxyl,
(3) halogen, and
(4) C$_{1-6}$alkyl;
R$^3$ is selected from the group consisting of:
(1) hydrogen,
(2) hydroxyl,
(3) halogen, and
(4) C$_{1-6}$alkyl;
R$^4$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C═O)—C$_{1-6}$alkyl,
(7) —NH$_2$,
(8) —NH—C$_{1-6}$alkyl,
(9) —NO$_2$,
(10) phenyl,
(11) heterocycle,
(12) —CO$_2$H, and
(13) —CN;
or a pharmaceutically acceptable salt thereof.

2. The compound of claim 1 of the formula Ia:

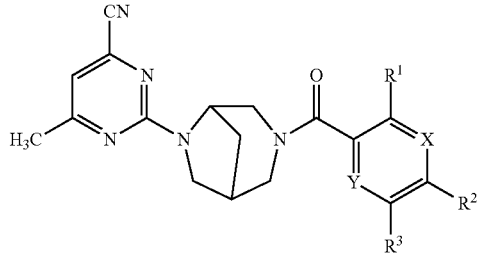

or a pharmaceutically acceptable salt thereof.

3. The compound of claim 1 of the formula Ib:

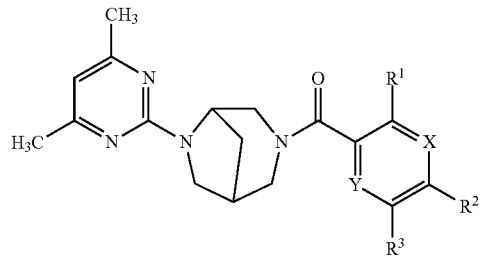

or a pharmaceutically acceptable salt thereof.

4. The compound of claim 1 or a pharmaceutically acceptable salt thereof wherein X is N.

5. The compound of claim 1 or a pharmaceutically acceptable salt thereof wherein X is CH.

6. The compound of claim 1 or a pharmaceutically acceptable salt thereof wherein R$^1$ is selected from the group consisting of:
(1) hydrogen,
(2) halogen,
(3) hydroxyl,
(4) C$_{1-6}$alkyl, which is unsubstituted or substituted with halogen, hydroxyl or phenyl,
(5) —O—C$_{1-6}$alkyl, which is unsubstituted or substituted with halogen, hydroxyl or phenyl,
(6) —CN, and
(7) heteroaryl, wherein heteroaryl is selected from imidazolyl, indolyl, oxazolyl, pyridyl, pyrrolyl, pyrimidinyl, tetrazolyl, and triazolyl, which is unsubstituted or substituted with halogen, hydroxyl, C$_{1-6}$alkyl, —O—C$_{1-6}$alkyl or —NO$_2$.

7. The compound of claim 1 or a pharmaceutically acceptable salt thereof wherein R$^1$ is independently selected from the group consisting of:
(1) hydrogen,
(2) fluoro,
(3) chloro,
(4) bromo,
(5) methyl,
(6) ethyl,
(7) methoxy,
(8) trifluoromethyl,
(9) trifluoromethoxy,
(10) difluoromethoxy,
(11) difluoroethoxy,
(12) trifluoroethoxy, and
(13) heteroaryl, wherein heteroaryl is selected from imidazolyl, indolyl, oxazolyl, pyridyl, pyrrolyl, pyrimidinyl, tetrazolyl, and triazolyl.

8. The compound of claim 1 or a pharmaceutically acceptable salt thereof wherein R$^2$ is hydrogen.

9. A compound which is selected from the group consisting of:
6-methyl-2-(3-(2-(2,2,2-trifluoroethyl)benzoyl)-3,6-diazabicyclo[3.2.1]-octan-6-yl)pyrimidine-4-carbonitrile;
2-(3-(2-(difluoromethoxy)benzoyl)-3,6-diazabicyclo[3.2.1]-octan-6-yl)-6-methylpyrimidine-4-carbonitrile;
6-methyl-2-(3-(2-(2,2,2-trifluoroethoxy)benzoyl)-3,6-diazabicyclo[3.2.1]octan-6-yl)pyrimidine-4-carbonitrile;
2-(3-{[2-(2,2-difluoroethoxy)pyridin-3-yl]carbonyl}-3,6-diazabicyclo[3.2.1]oct-6-yl)-6-methylpyrimidine-4-carbonitrile;
2-(3-(2-cyclopropylnicotinoyl)-3,6-diazabicyclo[3.2.1]octan-6-yl)-6-methylpyrimidine-4-carbonitrile;

2-(3-(2-(methoxymethyl)benzoyl)-3,6-diazabicyclo[3.2.1]octan-6-yl)-6-methylpyrimidine-4-carbonitrile;

6-methyl-2-(3-(2-((methylsulfonyl)methyl)benzoyl)-3,6-diazabicyclo[3.2.1]octan-6-yl)pyrimidine-4-carbonitrile;

(2-cyclopropyl-5-fluoropyridin-3-yl)(6-(4,6-dimethylpyridin-2-yl)-3,6-diazabicyclo[3.2.1]octan-3-yl)methanone;

(2-(2,2-difluoroethoxy)pyridin-3-yl)(6-(4,6-dimethylpyrimidin-2-yl)-3,6-diazabicyclo[3.2.1]octan-3-yl)methanone;

(6-(4,6-dimethylpyrimidin-2-yl)-3,6-diazabicyclo[3.2.1]octan-3-yl)(2-(methoxymethyl)phenyl)methanone;

3-[(2-cyclopropylphenyl)-carbonyl]-6-(4,6-dimethylpyrimidin-2-yl)-3,6-diazabicyclo[3.2.1]octane;

3-[(2-cyclopropyl-5-fluorophenyl)carbonyl]-6-(4,6-dimethylpyrimidin-2-yl)-3,6-diazabicyclo[3.2.1]octane;

3-[(2-cyclopropyl-6-methoxypyridin-3-yl)carbonyl]-6-(4,6-dimethylpyrimidin-2-yl)-3,6-diazabicyclo[3.2.1]octane;

3-[(2-cyclopropyl-4-fluorophenyl)carbonyl]-6-(4,6-dimethylpyrimidin-2-yl)-3,6-diazabicyclo[3.2.1]octane;

6-(4,6-dimethylpyrimidin-2-yl)-3-{[2-(trifluoromethoxy)-phenyl]carbonyl}-3,6-diazabicyclo[3.2.1]octane;

6-(4,6-dimethylpyrimidin-2-yl)-3-{[2-(1-methylethoxy)-phenyl]carbonyl}-3,6-diazabicyclo[3.2.1]octane;

6-(4,6-dimethylpyrimidin-2-yl)-3-{[2-(methylsulfanyl)-phenyl]carbonyl}-3,6-diazabicyclo[3.2.1]octane;

6-(4,6-dimethylpyrimidin-2-yl)-3-{[2-(1-fluorocyclopropyl)-phenyl]carbonyl}-3,6-diazabicyclo[3.2.1]octane;

6-(4,6-dimethylpyrimidin-2-yl)-3-{[2-(2H-tetrazol-2-yl)phenyl]carbonyl}-3,6-diazabicyclo[3.2.1]octane;

6-(4,6-dimethylpyrimidin-2-yl)-3-{[3-(1H-pyrazol-1-yl)pyrazin-2-yl]carbonyl}-3,6-diazabicyclo[3.2.1]octane;

6-(4,6-dimethylpyrimidin-2-yl)-3-{[2-(1-methylethoxy)pyridin-3-yl]carbonyl}-3,6-diazabicyclo[3.2.1]octane;

6-(4,6-dimethylpyrimidin-2-yl)-3-{[2-(2,2,2-trifluoroethoxy)pyridin-3-yl]carbonyl}-3,6-diazabicyclo[3.2.1]octane;

6-(4,6-dimethylpyrimidin-2-yl)-3-{[2-(5-methyl-1,2,4-oxadiazol-3-yl)pyridin-3-yl]carbonyl}-3,6-diazabicyclo[3.2.1]octane;

(2-cyclopropyl-3-fluorophenyl)(6-(4,6-dimethylpyrimidin-2-yl)-3,6-diazabicyclo[3.2.1]octan-3-yl)methanone;

6-(4,6-dimethylpyrimidin-2-yl)-3-{[2-(2,2,2-trifluoroethyl)phenyl]carbonyl}-3,6-diazabicyclo[3.2.1]octane;

6-(4,6-dimethylpyrimidin-2-yl)-3-{[2-(2,2,2-trifluoroethoxy)-phenyl]carbonyl}-3,6-diazabicyclo[3.2.1]octane;

6-(4,6-dimethylpyrimidin-2-yl)-3-[(2-propylphenyl)carbonyl]-3,6-diazabicyclo[3.2.1]octane;

6-(4,6-dimethylpyrimidin-2-yl)-3-({2-[(methylsulfonyl)methyl]phenyl}carbonyl)-3,6-diazabicyclo[3.2.1]octane;

1-(2-{[6-(4,6-dimethylpyrimidin-2-yl)-3,6-diazabicyclo[3.2.1]oct-3-yl]carbonyl}-phenyl)-cyclopropanecarbonitrile;

6-(4,6-dimethylpyrimidin-2-yl)-3-{[6-methoxy-2-(2H-1,2,3-triazol-2-yl)pyridin-3-yl]carbonyl}-3,6-diazabicyclo[3.2.1]octane;

6-(4,6-dimethylpyrimidin-2-yl)-3-{[2-(2H-1,2,3-triazol-2-yl)pyridin-3-yl]carbonyl}-3,6-diazabicyclo[3.2.1]octane;

6-(4,6-dimethylpyrimidin-2-yl)-3-{[2-(2,2,2-trifluoroethyl)pyridin-3-yl]carbonyl}-3,6-diazabicyclo[3.2.1]octane;

6-(4,6-dimethylpyrimidin-2-yl)-3-{[2-(2-methoxyethyl)-phenyl]carbonyl}-3,6-diazabicyclo[3.2.1]octane;

3-{[2-(difluoromethoxy)phenyl]carbonyl}-6-(4,6-dimethylpyrimidin-2-yl)-3,6-diazabicyclo[3.2.1]octane;

3-[(2-cyclopropylpyridin-3-yl)carbonyl]-6-(4,6-dimethylpyrimidin-2-yl)-3,6-diazabicyclo[3.2.1]octane;

3-{[2-(2,2-difluoroethyl)phenyl]carbonyl}-6-(4,6-dimethylpyrimidin-2-yl)-3,6-diazabicyclo[3.2.1]octane;

3-{[2-(2,2-difluoroethoxy)-phenyl]carbonyl}-6-(4,6-dimethylpyrimidin-2-yl)-3,6-diazabicyclo[3.2.1]octane;

3-[2-(cyclopentyloxy)pyridin-3-yl]-(6-(4,6-dimethylpyrimidin-2-yl)-3,6-diazabicyclo[3.2.1]octan-3-yl)methanone;

3-{[2-(cyclopropyl-methoxy)pyridin-3-yl]carbonyl}-6-(4,6-dimethylpyrimidin-2-yl)-3,6-diazabicyclo-[3.2.1]octane;

6-(4,6-dimethyl-pyrimidin-2-yl)-3-{[2-(2-methylpropoxy)pyridin-3-yl]carbonyl}-3,6-diazabicyclo[3.2.1]octane;

3-({2-[(2,2-difluorocyclopropyl)methoxy]pyridin-3-yl}carbonyl)-6-(4,6-dimethylpyrimidin-2-yl)-3,6-diazabicyclo[3.2.1]octane;

3-{[2-(cyclobutylmethoxy)pyridin-3-yl]carbonyl}-6-(4,6-dimethylpyrimidin-2-yl)-3,6-diazabicyclo[3.2.1]octane;

6-(4,6-dimethylpyrimidin-2-yl)-3-{[2-(2,2,3,3-tetrafluoropropoxy)pyridin-3-yl]carbonyl}-3,6-diazabicyclo[3.2.1]octane;

6-(4,6-dimethylpyrimidin-2-yl)-3-{[2-(3,3,3-trifluoropropoxy)pyridin-3-yl]carbonyl}-3,6-diazabicyclo[3.2.1]octane;

1-[(3-{[6-(4,6-dimethylpyrimidin-2-yl)-3,6-diazabicyclo[3.2.1]oct-3-yl]carbonyl}pyridin-2-yl)oxy]propan-2-ol;

(6-(4,6-dimethylpyrimidin-2-yl)-3,6-diazabicyclo[3.2.1]octan-3-yl)(2-((R)-3-methoxypyrrolidin-1-yl)pyridin-3-yl)methanone;

2-((2,2-difluoroethyl)(methylamino)pyridin-3-yl)(6-(4,6-dimethylpyridin-2-yl)-3,6-diazabicyclo[3.2.1]octan-3-yl)methanone;

(3-(cyclopropylmethoxy)pyrazin-2-yl)(6-(4,6-dimethylpyrimidin-2-yl)-3,6-diazabicyclo[3.2.1]octan-3-yl)methanone;

3-{[3-(2,2-difluoroethoxy)pyrazin-2-yl]carbonyl}-6-(4,6-dimethylpyrimidin-2-yl)-3,6-diazabicyclo[3.2.1]octane;

6-(4,6-dimethylpyrimidin-2-yl)-3-{[3-(2,2,2-trifluoroethoxy)pyrazin-2-yl]carbonyl}-3,6-diazabicyclo[3.2.1]octane;

(6-(4,6-dimethylpyrimidin-2-yl)-3,6-diazabicyclo[3.2.1]octan-3-yl)(3-(2,2,3,3-tetrafluoropropoxy)pyrazin-2-yl)methanone;

6-(4,6-dimethylpyrimidin-2-yl)-3-{[3-(1-methylethoxy)pyrazin-2-yl]carbonyl}-3,6-diazabicyclo[3.2.1]octane; and (3-(2,2-difluoropropoxy)pyrazin-2-yl)(6-(4,6-dimethylpyrimidin-2-yl)-3,6-diazabicyclo[3.2.1]octan-3-yl)methanone;

or a pharmaceutically acceptable salt thereof.

10. A pharmaceutical composition which comprises an inert carrier and a compound of claim 1 or a pharmaceutically acceptable salt thereof.

11. A method for enhancing the quality of sleep in a mammalian patient in need thereof which comprises administering to the patient a therapeutically effective amount of the compound of claim 1 or a pharmaceutically acceptable salt thereof.

12. A method for treating insomnia in a mammalian patient in need thereof which comprises administering to the patient a therapeutically effective amount of the compound of claim 1 or a pharmaceutically acceptable salt thereof.

* * * * *